US011697850B2

(12) United States Patent
Ridker et al.

(10) Patent No.: US 11,697,850 B2
(45) Date of Patent: *Jul. 11, 2023

(54) POLYMORPHISM IN THE APO(A) GENE PREDICT RESPONSIVENESS TO ACETYLSALICYLIC ACID TREATMENT

(71) Applicants: Celera Corporation, Alameda, CA (US); The Brigham and Women's Hospital, Inc., Boston, MA (US)

(72) Inventors: Paul M. Ridker, Chestnut Hill, MA (US); Daniel Chasman, Cambridge, MA (US); Dov Shiffman, Palo Alto, CA (US)

(73) Assignees: The Brigham and Women's Hospital, Inc., Boston, MA (US); Celera Corporation, Alameda, CA (US)

( * ) Notice: Subject to any disclaimer, the term of this patent is extended or adjusted under 35 U.S.C. 154(b) by 369 days.

This patent is subject to a terminal disclaimer.

(21) Appl. No.: 16/716,193

(22) Filed: Dec. 16, 2019

(65) Prior Publication Data

US 2020/0248262 A1 Aug. 6, 2020

Related U.S. Application Data

(63) Continuation of application No. 15/477,206, filed on Apr. 3, 2017, now Pat. No. 10,550,433, which is a continuation of application No. 14/534,516, filed on Nov. 6, 2014, now abandoned, which is a continuation of application No. 13/741,750, filed on Jan. 15, 2013, now abandoned, which is a continuation of application No. 13/090,116, filed on Apr. 19, 2011, now abandoned, which is a continuation of application No. 12/118,060, filed on May 9, 2008, now Pat. No. 7,943,317.

(60) Provisional application No. 60/916,858, filed on May 9, 2007.

(51) Int. Cl.
| | | |
|---|---|---|
| C07H 21/04 | (2006.01) | |
| C12Q 1/68 | (2018.01) | |
| C12Q 1/6883 | (2018.01) | |
| G01N 33/92 | (2006.01) | |
| A61K 31/616 | (2006.01) | |
| C12Q 1/6876 | (2018.01) | |

(52) U.S. Cl.
CPC .......... *C12Q 1/6883* (2013.01); *A61K 31/616* (2013.01); *C12Q 1/6876* (2013.01); *G01N 33/92* (2013.01); *C12Q 2600/106* (2013.01); *C12Q 2600/136* (2013.01); *C12Q 2600/156* (2013.01); *C12Q 2600/158* (2013.01); *C12Q 2600/172* (2013.01); *G01N 2333/775* (2013.01); *G01N 2500/04* (2013.01); *G01N 2800/32* (2013.01); *G01N 2800/50* (2013.01); *G01N 2800/52* (2013.01)

(58) Field of Classification Search
None
See application file for complete search history.

(56) References Cited

U.S. PATENT DOCUMENTS

| | | | |
|---|---|---|---|
| 3,798,220 A | 3/1974 | Klemm et al. | |
| 7,625,699 B2 * | 12/2009 | Devlin | C12Q 1/6883 536/23.1 |
| 7,781,168 B2 * | 8/2010 | Lakoubova | C12Q 1/6883 536/24.31 |
| 7,943,317 B2 * | 5/2011 | Ridker | C12Q 1/6876 536/23.1 |
| 10,550,433 B2 * | 2/2020 | Ridker | A61P 9/10 |
| 2005/0272054 A1 | 12/2005 | Cargill et al. | |
| 2005/0287558 A1 | 12/2005 | Crooke et al. | |
| 2006/0199239 A1 | 9/2006 | Gurbel | |
| 2007/0031847 A1 * | 2/2007 | Cargill | C12Q 1/6883 536/23.2 |
| 2007/0099242 A1 | 5/2007 | Heinecke et al. | |
| 2010/0009005 A1 * | 1/2010 | Soula | A61P 7/02 424/490 |
| 2010/0120045 A1 * | 5/2010 | Helgadottir | C12Q 1/6883 435/6.1 |
| 2011/0206667 A1 | 8/2011 | Ridker et al. | |
| 2014/0024623 A1 | 1/2014 | Ridker et al. | |
| 2015/0284799 A1 | 10/2015 | Ridker et al. | |
| 2017/0335394 A1 | 11/2017 | Ridker et al. | |

FOREIGN PATENT DOCUMENTS

| | | |
|---|---|---|
| CA | 2 566 257 A1 | 11/2005 |
| EP | 1293510 A1 | 3/2003 |
| WO | WO 04/058052 A2 | 7/2004 |

OTHER PUBLICATIONS

Danik et al. (JAMA, vol. 296, No. 11, pp. 1363-1370, Sep. 2006). (Year: 2006).*
Shiftman et al. Thromb Haemost, vol. 102, pp. 1-2, 2009) (Year: 2009).*
Cavallari et al. Current Treatment Options in Cardiovascular Medicine, vol. 11, pp. 191-200, 2009 (Year: 2009).*
Cavallari et al. (Ann Pharmacother, vol. 40, pp. 812-817, 2006) (Year: 2006).*
Yusuke (NCBI SNP database, rs3798220, Aug. 12, 2002).*
Sobrino et al. (Forensic Science International, vol. 154, pp. 181-194, 2005). (Year: 2005).*
EP 08754317.9, dated Jan. 24, 2011, Extended European Search Report.
PCT/US2008/005986, dated Nov. 9, 2009, International Preliminary Report on Patentability.
PCT/US2008/005986, dated Sep. 2, 2008, International Search Report and Written Opinion.

(Continued)

*Primary Examiner* — Jeanine A Goldberg
(74) *Attorney, Agent, or Firm* — Wolf, Greenfield & Sacks, P.C.

(57) ABSTRACT

This invention relates to nucleotide polymorphisms in the human Apo(a) gene and to the use of Apo(a) nucleotide polymorphisms in identifying whether a human subject will respond or not to treatment with acetylsalicylic acid.

16 Claims, 7 Drawing Sheets

Specification includes a Sequence Listing.

(56) References Cited

OTHER PUBLICATIONS

Akaike et al., Effect of aspirin treatment on serum concentrations of lipoprotein(a) in patients with atherosclerotic diseases. Clin Chem. Sep. 2002;48(9):1454-9.
Alpert et al., Issues in antithrombin therapy for UA/NSTEMI. Eur Heart J Suppl. 2001; 3:J15-J23.
Ascend Study Collaborative Group—Bowman et al., Effects of Aspirin for Primary Prevention in Persons with Diabetes Mellitus. N Engl J Med. Oct. 18, 2018;379(16):1529-1539. doi: 10.1056/NEJMoa1804988. Epub Aug. 26, 2018.
Cavallari et al., Genomics and the efficacy of aspirin in the treatment of cerebrovascular disease. Curr Treat Options Cardiovasc Med. Jun. 2009;11(3):191-200.
Cavallari et al., Sex difference in the antiplatelet effect of aspirin in patients with stroke. Ann Pharmacother. May 2006;40(5):812-7. Epub Apr. 11, 2006.
Chasman et al., Polymorphism in the apolipoprotein(a) gene, plasma lipoprotein(a), cardiovascular disease, and low-dose aspirin therapy. Atherosclerosis. Apr. 2009;203(2):371-6. Epub ahead of print Jul. 26, 2008.
Clarke et al., Genetic variants associated with Lp(a) lipoprotein level and coronary disease. N Engl J Med. Dec. 24, 2009;361(26):2518-28. doi: 10.1056/NEJMoa0902604.
Danick et al., Lipoprotein(a), measured with an assay independent of apolipoprotein(a) isoform size, and risk of future cardiovascular events among initially healthy women. JAMA. Sep. 20, 2006;296(11):1363-70.
Dardik et al., A quantitative assay for the non-covalent association between apolipoprotein[a] and apolipoprotein B: an alternative measure of Lp[a] assembly. J Lipid Res. Jun. 2000;41(6):1013-9.
Eisenstein et al., Clopidogrel use and long-term clinical outcomes after drug-eluting stent implantation. JAMA. Jan. 10, 2007;297(2):159-68. Epub Dec. 5, 2006.
Emerging Risk Factors Collaboration—Erqou et al., Lipoprotein(a) concentration and the risk of coronary heart disease, stroke, and nonvascular mortality. JAMA. Jul. 22, 2009;302(4):412-23. doi:10.1001/jama.2009.1063. Review.
Helgadottir et al., Apolipoprotein(a) genetic sequence variants associated with systemic atherosclerosis and coronary atherosclerotic burden but not with venous thromboembolism. J Am Coll Cardiol. Aug. 21, 2012;60(8):722-9. doi:10.1016/j.jacc.2012.01.078.
Kagawa et al., Aspirin reduces apolipoprotein(a) (apo(a)) production in human hepatocytes by suppression of apo(a) gene transcription. J Biol Chem. Nov. 26, 1999;274(48):34111-5.
Lev et al., Genetic polymorphisms of the platelet receptors P2Y(12), P2Y(1) and GP IIIa and response to aspirin and clopidogrel. Thromb Res. 2007;119(3):355-60. Epub Mar. 6, 2006.
Luke et al., A polymorphism in the protease-like domain of apolipoprotein(a) is associated with severe coronary artery disease. Arterioscler Thromb Vasc Biol. Sep. 2007;27(9):2030-6. Epub Jun. 14, 2007.
Mar. 2006 assembly—NCBI build 36.1; rs3798220 dbSNP @ NCBI. Printed Aug. 26, 2008. Best available copy.
Mousa et al., Ximelagatran, the new oral anticoagulant: would warfarin survive the challenge? Cardiovasc Drug Rev. 2005 Winter;23(4):331-44.
NCBI build 128; rs9457927 dbSNP @NCBI (2006). Printed Aug. 26, 2008. Best available copy.
NCBI build 128; rs9457931 dbSNP @ NCBI (2006). Printed Aug. 26, 2008. Best available copy.
NCBI SNP database. rs3798220. Printed Dec. 15, 2010.
NCBI SNP database. rs9457927. Printed Dec. 15, 2010.
NCBI SNP database. rs9457931. Printed Dec. 15, 2010.
Nordestgaard et al., Lipoprotein (a) as a cause of cardiovascular disease: insights from epidemiology, genetics, and biology. J Lipid Res. Nov. 2016;57(11):1953-1975. Epub Sep. 27, 2016. Review.
Onishi et al., Causes and Pathologies of Diseases: The Genetic Analysis of Myocardial Infarctions. In: Annual Review Circulatory Organs. Jan. 20, 2004. Yazaki et al., Eds. pp. 53-56.
Ridker et al., A randomized trial of low-dose aspirin in the primary prevention of cardiovascular disease in women. N Engl J Med. Mar. 31, 2005;352(13):1293-304. Epub Mar. 7, 2005.
Schulman et al., Secondary prevention of venous thromboembolism with the oral direct thrombin inhibitor ximelagatran. N Engl J Med. Oct. 30, 2003;349(18):1713-21.
Shiffman et al., Aspirin use in the atherosclerosis risk in communities (aric) study attenuated the risk of coronary heart disease associated with an apolipoprotein(a) variant. Arterioscler Thromb Vasc Biol. Jul. 2009;29(7):e10.
Shiffman et al., Coronary heart disease risk, aspirin use, and apolipoprotein(a) 4399Met allele in the Atherosclerosis Risk in Communities (ARIC) study. Thromb Haemost. Jul. 2009;102(1):179-80.
Sotos et al., The transitivity misconception of pearson's correlation coefficient. Statistics Education Research Journal. Nov. 2009; 8(2): 33-35.
Steering Committee of the Physicians' Health Study Research Group, Final report on the aspirin component of the ongoing Physicians' Health Study. N Engl J Med. Jul. 20, 1989;321(3):129-35.
Suk Danik et al., Lipoprotein(a), measured with an assay independent of apolipoprotein(a) isoform size, and risk of future cardiovascular events among initially healthy women. JAMA. Sep. 20, 2006;296(11):1363-70.
Virani et al., Associations between lipoprotein(a) levels and cardiovascular outcomes in black and white subjects: the Atherosclerosis Risk in Communities (ARIC) Study. Circulation. Jan. 17, 2012;125(2):241-9. doi: 10.1161/CIRCULATIONAHA.111.045120. Epub Nov. 29, 2011.

* cited by examiner

POLYMORPHISM IN THE APO(A) GENE PREDICT RESPONSIVENESS TO ACETYLSALICYLIC ACID TREATMENT

RELATED APPLICATION

This application is a continuation of U.S. application Ser. No. 15/477,206, filed on Apr. 3, 2017, which is a continuation of U.S. application Ser. No. 14/534,516, filed on Nov. 6, 2014, now abandoned, which is a continuation of U.S. patent application Ser. No. 13/741,750, filed Jan. 15, 2013, now abandoned, which is a continuation of U.S. patent application Ser. No. 13/090,116, filed Apr. 19, 2011, now abandoned, which is a continuation of U.S. patent application Ser. No. 12/118,060 filed May 9, 2008, now U.S. Pat. No. 7,943,317, which claims the benefit under 35 U.S.C. § 119(e) of U.S. provisional patent application No. 60/916,858, filed May 9, 2007, the disclosures of all of which are incorporated herein by reference.

GOVERNMENT LICENSE RIGHTS

This invention was made with government support under grant numbers HL 043851 and CA 047988 awarded by the National Institutes of Health. The government has certain rights in this invention.

FIELD OF THE INVENTION

The invention relates to methods for analyzing nucleotide variations in the apolipoprotein(a) (Apo(a)) gene to evaluate a human subject's responsiveness to acetylsalicylic acid therapy.

BACKGROUND

Lipoprotein(a) (Lp(a)) is a plasma complex that consists of a single apolipoprotein(a) (Apo(a)) molecule covalently linked through a disulfide bond to a single apolipoprotein B-100 molecule together with cholesterol-rich lipid (Marcovina et al. in *Handbook of lipoprotein testing* Rifai et al. Eds.: AACC Press, Washington, D.C., 2000; p. 819). While the biological functions of Lp(a) in normal physiology remain uncertain, high levels of Lp(a) have been associated with increased cardiovascular risk and cardiovascular events such as myocardial infarction and stroke, particularly when LDL-C is also elevated (Berglund et al., *Arterioscler Thromb Vasc Biol* 24, 2219 (2004); Hobbs et al., *Curr Opin Lipidol* 10, 225 (1999); Danesh et al., *Circulation* 102, 1082 (2000); Ridker et al., *JAMA* 297, 611 (2007); Danik et al., *JAMA* 296, 1363 (2006)).

The apolipoprotein(a) locus is among the most polymorphic in the human genome. Apo(a) genetic variation has been associated with the wide range of Lp(a) levels and largely accounts for the heritability of Lp(a) (Broeckel et al., *Nat Genet* 30, 210 (2002); Boerwinkle et al., *J Clin Invest* 90, 52 (1992); Mooser et al., *Am J Hum Genet* 61, 402 (1997); Schmidt et al., *Eur J Hum Genet* 14 190 (2006)). Recently, several single nucleotide polymorphisms (SNPs) in the Apo(a) gene were identified and have been associated with cardiovascular disorders such as myocardial infarction and stroke and/or drug response such as response to statins (See U.S. Patent Application Publication US2005/0272054A1).

Subjects at increased risk of future cardiovascular events are often prescribed acetylsalicylic acid (aspirin) to reduce the risk of a cardiovascular event. However, acetylsalicylic acid is not effective in all subjects and the use of acetylsalicylic acid (aspirin) as primary prevention against cardiovascular events has been controversial, particularly in women, for whom there have been few data (Ridker et al., *N Engl J Med* 352, 1293; 2005).

Thus, there is a continuing need to improve pharmaceutical agent selection design and therapy. In that regard, SNPs can be used to identify patients most suited to treatment with particular pharmaceutical agents such as acetylsalicylic acid and/or other anti-platelet and/or antithrombotic agents (this is often termed "pharmacogenetics"). Similarly, SNPs can be used to exclude patients from certain treatments due to the patient's increased likelihood of developing toxic side effects or their likelihood of not responding to the treatment. By doing so, such SNPs could be useful in defining the benefit to risk ratio of a given intervention for individual subjects. Pharmacogenetics can also be used in pharmaceutical research to assist the drug development and selection process. (Linder et al., *Clinical Chemistry*, 43, 254 (1997); Marshall, *Nature Biotechnology*, 15, 1249 (1997); International Patent Application WO 97/40462, Spectra Biomedical; and Schafer et al., *Nature Biotechnology*, 16, 3(1998)).

SUMMARY OF THE INVENTION

The present invention relates, in part, to methods of evaluating a human subject's response to acetylsalicylic acid treatment to reduce the risk of a future cardiovascular event. The invention is based, in part, on the finding that novel nucleotide polymorphisms in the Apo(a) gene allow an inference to be drawn as to whether a human subject will respond or not to treatment with acetylsalicylic acid, a particular dose of acetylsalicylic acid, or to another anti-platelet or antithrombotic agent. The invention permits identifying subjects who will respond and subjects who will not respond to treatment with acetylsalicylic acid prior to initiation of therapy. The invention also permits selecting among anti-platelet and antithrombotic agents the agents most likely to offer the highest benefit of lowering risk of a cardiovascular event for a particular subject. The polymorphisms disclosed are also useful as targets for the design of diagnostic reagents and the development of therapeutic agents for use in the diagnosis and treatment of cardiovascular events and related pathologies.

According to one aspect of the invention, a method is provided for evaluating a human subject's responsiveness to acetylsalicylic acid treatment to reduce the risk of a future cardiovascular event. The method involves determining the identity of a single nucleotide polymorphism at position chromosome 6:160880877 (March 2006 assembly—NCBI build 36.1; rs3798220 dbSNP @ NCBI) of the human subject's apolipoprotein(a) (Apo(a)) gene. In some important embodiments, the presence of a polymorphism characterized by cytosine or guanine at the position chromosome 6:160880877 indicates responsiveness to acetylsalicylic acid treatment. In other important embodiments, the presence of a polymorphism characterized by thymine or adenine at the position chromosome 6:160880877 indicates non-responsiveness to acetylsalicylic acid treatment.

Any of a variety of detection methods may be employed, as will be well known to those of ordinary skill in the art. Common methods include contacting a nucleic acid obtained from the subject with a nucleic acid probe or sequencing a nucleic acid obtained from the subject. Examples of such methods include but are not limited to allele-specific probe hybridization, allele-specific primer extension, allele-specific amplification, 5' nuclease digestion, molecular beacon assay, oligonucleotide ligation assay, size analysis, and single-stranded conformation polymorphism. In some important embodiments, the identity of the polymorphism is determined by sequencing a nucleic acid obtained from the subject.

According to another aspect of the invention, an assay is provided. The assay involves contacting an agent with an isolated Apo(a) protein encoded by an Apo(a) gene having nucleotide cytosine or guanine at chromosome 6:160880877 (March 2006 assembly-NCBI build 36.1; rs3798220 dbSNP @ NCBI), evaluating binding of the agent to the isolated Apo(a) protein or to Lipoprotein(a) (Lp(a)), and comparing the binding to a control. In some embodiments, the control involves a measurement of binding of a acetylsalicylic acid to the isolated Apo(a) protein or to Lp(a), or to platelets or a measurement of acetylsalicylic acid interaction with platelets.

According to another aspect of the invention, an assay is provided. The assay involves contacting an agent with an isolated Apo(a) protein encoded by an Apo(a) gene having nucleotide thymine or adenine at chromosome 6:160880877 (March 2006 assembly-NCBI build 36.1; rs3798220 dbSNP @ NCBI), evaluating binding of the agent to the isolated Apo(a) protein, and comparing the binding to a control. In some embodiments, the control involves a measurement of binding of a acetylsalicylic acid to the isolated Apo(a) protein or to Lp(a), or to platelets or a measurement of acetylsalicylic acid interaction with platelets.

According to another aspect of the invention, a method of treatment is provided. The method involves selecting a human subject on the basis that the human subject has an Apo(a) polymorphism characterized by cytosine or guanine at chromosome 6:160880877 (March 2006 assembly—NCBI build 36.1; rs3798220 dbSNP @ NCBI) and administering to the subject acetylsalicylic acid for reducing the risk of a future cardiovascular event because the subject has the polymorphism. In some embodiments, the subject also has an elevated level of Lp(a) in the blood.

According to another aspect of the invention, a method of treatment is provided. The method involves selecting a human subject on the basis that the human subject has an Apo(a) polymorphism characterized by thymine or adenine at chromosome 6:160880877 (March 2006 assembly—NCBI build 36.1; rs3798220 dbSNP @ NCBI) and administering to the subject an antithrombotic agent other than acetylsalicylic acid for reducing the risk of a future cardiovascular event because the subject has the polymorphism. In some embodiments, the subject also has an elevated level of Lp(a) in the blood.

The antithrombotic agent may be a thienopyridine or a thienopyridine derivative. Examples of thienopyridine or thienopyridine derivatives include but are not limited to clopidogrel, clopidogrel bisulfate, ticlopidine, prasugrel (CS-747, or LY 640315), SR 25989, and PCR 4099. Antithrombotic agents also include but are not limited to cenoxaparin sodium, ximelagatran, abciximab, otirofiban. Examples of other antithrombotic agents also include plasminogen activator (e.g., Activase, Alteplase) (catalyzes the conversion of inactive plasminogen to plasmin. This may occur via interactions of prekallikrein, kininogens, Factors XII, Mina, plasminogen proactivator, and tissue plasminogen activator TPA), Streptokinase, Urokinase, Anisoylated Plasminogen-Streptokinase Activator Complex, Pro-Urokinase, (Pro-UK), rTPA (alteplase or activase; r denotes recombinant), rPro-UK, Abbokinase, Eminase, Sreptase, Anagrelide, Anagrelide Hydrochloride, Bivalirudin, Dalteparin Sodium, Danaparoid Sodium, Dazoxiben Hydrochloride, Efegatran Sulfate, Enoxaparin Sodium, Ifetroban, Ifetroban Sodium, Tinzaparin Sodium, retaplase, Trifenagrel, Warfarin, Dextrans, aminocaproic acid (Amicar), and tranexamic acid (Amstat), Sulfinpyrazone, Dipyridamole, Clofibrate, Pyridinol Carbamate, PGE, Glucagon, Antiserotonin drugs, Caffeine, Theophyllin Pentoxifyllin, and Ticlopidine. Antithrombotic agents also include those that specifically bind to platelet receptors including but not limited to the PAR-1 and PAR-2 receptors, as well as platelet receptors for thrombin, and the platelet ADP receptors such as $P2Y_{12}$.

According to another aspect of the invention, a method is provided for evaluating a human subject's responsiveness to acetylsalicylic acid treatment to reduce the risk of a future cardiovascular event. The method involves detecting the presence or absence of a genetic marker linked or in linkage disequilibrium with a single nucleotide polymorphism (SNP) at position chromosome 6:160880877 (March 2006 assembly—NCBI build 36.1; rs3798220 dbSNP @ NCBI) of the human subject's apolipoprotein(a) (Apo(a)) gene. The genetic marker may be an allele, a SNP, a restriction fragment length polymorphism (RFLP), a random amplified polymorphic DNA (RAPD), an amplified fragment length polymorphism (AFLP), or a simple sequence repeat (SSR). In some embodiments, the genetic marker is a SNP at position chromosome 6:160849894 (NCBI build 128; rs9457931 dbSNP@NCBI). In some embodiments, the genetic marker is a SNP at position chromosome 6:160830272 (NCBI build 128; rs9457927 dbSNP@NCBI). In some embodiments, the linkage is between 16, 17, or 18 repeats of Kringle (Kr) IV type 2 domain.

In some important embodiments, the presence of a polymorphism characterized by cytosine or guanine at the position chromosome 6:160880877 indicates responsiveness to acetylsalicylic acid. In other important embodiments, the presence of a polymorphism characterized by thymine or adenine at the position chromosome 6:160880877 indicates non-responsiveness to acetylsalicylic acid. In some embodiments, the method further involves determining a level of Lipoprotein(a) (Lp(a)) in a blood sample from the subject.

According to yet another aspect of the invention, a method of treatment is provided. The method involves selecting a human subject on the basis that the human subject has a genetic marker linked or in linkage disequilibrium with an Apo(a) polymorphism characterized by cytosine or guanine at chromosome 6:160880877 (March 2006 assembly—NCBI build 36.1; rs3798220 dbSNP @ NCBI) and administering to the subject acetylsalicylic acid for reducing the risk of a future cardiovascular event because the subject has the polymorphism.

The genetic marker may be an allele, a SNP, a restriction fragment length polymorphism (RFLP), a random amplified polymorphic DNA (RAPD), an amplified fragment length polymorphism (AFLP), or a simple sequence repeat (SSR). In some embodiments, the human subject also has an elevated level of Lipoprotein(a) (Lp(a)) in the blood.

In some embodiments, the genetic marker is a SNP at position chromosome 6:160849894 (NCBI build 128; rs9457931 dbSNP@NCBI). In some embodiments, the genetic marker is a SNP at position chromosome 6:160830272 (NCBI build 128; rs9457927 dbSNP@NCBI). In some embodiments, the linkage is between 16, 17, or 18 repeats of Kringle (Kr) IV type 2 domain.

According to yet another aspect of the invention, a method of treatment is provided. The method involves selecting a human subject on the basis that the human subject has a genetic marker linked or in linkage disequilibrium with an Apo(a) polymorphism characterized by thymine or adenine at chromosome 6:160880877 (March 2006 assembly—NCBI build 36.1; rs3798220 dbSNP @ NCBI), and administering to the subject an antithrombotic agent other than acetylsalicylic acid for reducing the risk of a future cardiovascular event because the subject has the polymorphism. In some embodiments, the human subject also has an elevated level of Lipoprotein(a) (Lp(a)) in the blood.

The genetic marker may be an allele, a SNP, a restriction fragment length polymorphism (RFLP), a random amplified polymorphic DNA (RAPD), an amplified fragment length polymorphism (AFLP), or a simple sequence repeat (SSR). In some embodiments, the human subject also has an elevated level of Lipoprotein(a) (Lp(a)) in the blood.

According to still another aspect of the invention, a method is provided for evaluating a human subject's risk of a future cardiovascular event. The method involves determining the identity of a single nucleotide polymorphism at position chromosome 6:160880877 (March 2006 assembly—NCBI build 36.1; rs3798220 dbSNP @ NCBI) of the human subject's Apo(a) gene, and determining a level of Lipoprotein(a) (Lp(a)) in a blood sample from the human subject. In some embodiments, the presence of a polymorphism characterized by cytosine or guanine at the position chromosome 6:160880877 (March 2006 assembly—NCBI build 36.1; rs3798220 dbSNP @ NCBI) of the human subject's Apo(a) gene and the presence of an elevated level of Lp(a) in the blood sample from the subject indicates that the subject is at an elevated risk of a future cardiovascular event.

The following embodiments apply equally to the various aspects of the invention set forth herein unless indicated otherwise.

The cardiovascular event may be myocardial infarction, stroke, acute coronary syndrome, myocardial ischemia, chronic stable angina pectoris, unstable angina pectoris, cardiovascular death, coronary re-stenosis, coronary stent re-stenosis, coronary stent re-thrombosis, revascularization, angioplasty, transient ischemic attack, pulmonary embolism, vascular occlusion, or venous thrombosis.

In some embodiments, the method further involves determining a level of Lp(a) in a blood sample from the subject. In some embodiments, the subject has an elevated level of Lp(a) in the blood. The level of Lp(a) may be about 10 mg/dl or higher, about 15 mg/dl or higher, about 20 mg/dl or higher, about 25 mg/dl or higher, about 30 mg/dl or higher, about 35 mg/dl or higher, about 40 mg/dl or higher, about 45 mg/dl or higher, about 50 mg/dl or higher in the blood sample from the subject. Any of a variety of methods may be employed for determining the level of Lp(a). Such methods are known to those of ordinary skill in the art. An example of a method for determining the level of Lp(a) is described by Danik et al., *JAMA* 296, 1363 (2006).

These and other aspects of the invention are described in greater detail below.

BRIEF DESCRIPTION OF THE DRAWINGS

FIG. 1A) Lp(a) levels among Caucasian female study participants from the WHS (median=10.3 mg/dL), FIG. 1B) Lp(a) levels as in FIG. 1A) among the three genotypes of rs3798220. The inter-quartile ranges (IQR) and medians for the three genotypes are indicated by the boxes and their mid-lines. The whiskers span the range of Lp(a) values as far as 1.5 times the IQR from the median, and extreme Lp(a) values beyond the whiskers are indicated by circles. FIG. 1C) Lp(a) levels for Caucasian women with heterozygous genotype (median=79.3 mg/dL). Models for the distribution of Lp(a) in subpopulations with low Lp(a) and high Lp(a) are indicated by the fitted log-normal and normal distributions, respectively. FIG. 1D) Lp(a) distribution among Caucasian males from the PHS with heterozygous genotype for rs3798220 (median=66.9 mg/dL, measured with a different assay than for the samples from the WHS, see methods).

FIG. 3A) top histogram shows N Alleles vs. N Kr. IV, TYPE 2 Repeats, while bottom histogram shows fr. Alleles vs. N Kr. IV Type 2 Repeats according to genotype. FIG. 3B) N Alleles vs. N Kr. IV, TYPE 2 Repeats according to genotype.

DETAILED DESCRIPTION OF THE INVENTION

Figure 1A:
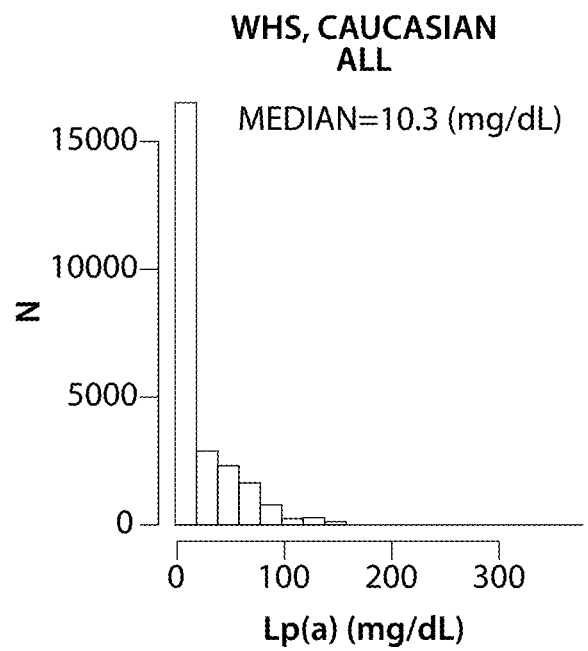
FIGS. 1A to 1D are sets of graphs showing the relation between the Lp(a) and rs3798220 genotype.

The invention relates, in part, to SNPs in the Apo(a) gene that are associated with a subject's responsiveness to acetylsalicylic acid treatment to reduce the risk of a future cardiovascular event. The invention also relates to the use of the polymorphism in the Apo(a) gene alone or in combination with a level of Lipoprotein (a) (Lp(a)) for evaluating a human subject's response to acetylsalicylic acid treatment and to methods of treatment based thereon. The invention is also directed to identifying and designing novel antithrombotic agents.

As used herein, the term "evaluate" or "evaluating", when used in reference to a subject's responsiveness to acetylsalicylic acid treatment, means drawing a conclusion about response to acetylsalicylic acid treatment using a process of analyzing the identity of a nucleotide at position chromosome 6:160880877 (March 2006 assembly—NCBI build 36.1; rs3798220 dbSNP @ NCBI) of the human subject's Apo(a) gene in a nucleic acid sample of the subject, and comparing the occurrence of the single nucleotide polymorphism (SNP) to known relationships of nucleotide occurrence(s) at position chromosome 6:160880877 (March 2006 assembly—NCBI build 36.1; rs3798220 dbSNP @ NCBI). The nucleotide occurrence can be identified directly by examining nucleic acid molecules, or indirectly by examining a polypeptide encoded by the Apo(a) gene.

Responsiveness to acetylsalicylic acid treatment means that, in an otherwise statistically similar pool of subjects, a subject on acetylsalicylic acid treatment who has a polymorphism characterized by cytosine or guanine at the position chromosome 6:160880877 (March 2006 assembly—NCBI build 36.1; rs3798220 dbSNP @ NCBI) of the human subject's apolipoprotein(a) (Apo(a)) gene is less likely to have a future cardiovascular event than a subject who is not on acetylsalicylic acid treatment.

In the context of the flanking sequences, the allele that is associated with acetylsalicylic acid responsiveness at the position chromosome 6:160880877 (March 2006 assembly—NCBI build 36.1; rs3798220 dbSNP @ NCBI) is, according to the University of California at Santa Cruz Genome Browser:

(SEQ ID NO: 1)
5'-GCTCCAAGAACAGCCTAGACACTTC C ATTTCCTGAACATGAGATT CGAGGT-3'

(SEQ ID NO: 2)
3'-CGAGGTTCTTGTCGGATCTGTGAAG G TAAAGGACTTGTACTCTAA GCTCCA-5'

(The plus ("+") strand is the top strand and the minus ("−") strand is the bottom strand)

The allele that is associated with acetylsalicylic acid non-responsiveness at the position chromosome 6:160880877 (March 2006 assembly—NCBI build 36.1; rs3798220 dbSNP @ NCBI is, according to the University of California at Santa Cruz Genome Browser:

(SEQ ID NO: 3)
5'-GCTCCAAGAACAGCCTAGACACTTC T ATTTCCTGAACATGAGATT CGAGGT-3'

(SEQ ID NO: 4)
3'-CGAGGTTCTTGTCGGATCTGTGAAG A TAAAGGACTTGTACTCTAA GCTCCA-5'

(The plus ("+") strand is the top strand and the minus ("−") strand is the bottom strand)

The Apo (a) gene SNP is described in U.S. Patent Application Publication US2005272054 under the designation rs3798220 hCV25930271. The Apo (a) gene SNP may also be found by a match of the primer sequence CGAATCT-CATGTTCAGGAAAATA (SEQ ID NO:5) described in U.S. Patent Application Publication US2005/0272054A1 the entire contents of which are incorporated by reference herein.

The term human subject includes a human who has had a cardiovascular event, is suspected of developing a cardiovascular event, or an asymptomatic subject who may be predisposed or at risk of a future cardiovascular event. Thus, in some embodiments, the human subject already has had a primary (first) cardiovascular event, such as, for example, a myocardial infarct or has had an angioplasty. A human subject who has had a primary cardiovascular event is at an elevated risk of a secondary (second) cardiovascular event. In some embodiments, the human subject has not had a primary cardiovascular event, but is at an elevated risk of having a cardiovascular event because the human subject has one or more risk factors to have a cardiovascular event. In some embodiments, the subject is already on treatment with a therapy for reducing the risk of a future cardiovascular event. The therapy can be any of the therapeutic agents referred to below. In still other embodiments, the subject has had a primary cardiovascular event and has one or more other risk factors. In some embodiments, the human subject is on therapy (e.g. on anti-lipemic therapy such as statin therapy) to reduce the risk of a future cardiovascular event. In some embodiments, the human subject is in the midst of an acute coronary syndrome and treatment decisions are being made to both manage the immediate cardiovascular event and to prevent event recurrences.

Examples of risk factors for a cardiovascular event include: hyperlipidemia, obesity, diabetes mellitus, hypertension, pre-hypertension, elevated level(s) of a marker of systemic inflammation, age, a family history of cardiovascular events, and cigarette smoking. The degree of risk of a cardiovascular event depends on the multitude and the severity or the magnitude of the risk factors that the human subject has. Risk charts and prediction algorithms are available for assessing the risk of cardiovascular events in a human subject based on the presence and severity of risk factors. One such example is the Framingham Heart Study risk prediction score. The human subject is at an elevated risk of having a cardiovascular event if the subject's 10-year calculated Framingham Heart Study risk score is greater than 5%, 6%, 7%, 8%, 9%, 10%, 11%, 12%, 13%, 14%, 15%, 16%, 17%, 18%, 19%, or 20%.

Another method for assessing the risk of a cardiovascular event in a human subject is a global risk score that incorporates a measurement of a level of a marker of systemic inflammation, such as CRP, into the Framingham Heart Study risk prediction score. Other methods of assessing the risk of a cardiovascular event in a human subject include coronary calcium scanning, cardiac magnetic resonance imaging, and/or magnetic resonance angiography (Ridker et al., *JAMA* 297, 611, 2007).

Hyperlipidemia is hypercholesterolemia and/or hypertriglyceridemia. Hypercholesterolemic human subjects and hypertriglyceridemic human subjects are at an increased incidence of cardiovascular events. A hypercholesterolemic human subject is one who fits the current criteria established for a hypercholesterolemic human subject. A hypertriglyceridemic human subject is one who fits the current criteria established for a hypertriglyceridemic subject. A hypercholesterolemic subject has an LDL level of >160 mg/dL, or an LDL level >130 mg/dL and at least two risk factors selected from the group consisting of: male gender, family history of premature coronary heart disease, cigarette smoking, hypertension, low HDL (<35 mg/dL), diabetes mellitus, hyperinsulinemia, abdominal obesity, high lipoprotein, and personal history of a cardiovascular event. A hypertriglyceridemic human subject has a triglyceride (TG) level of ≥250 mg/dL.

Hypertension is defined as a systolic blood pressure >140 mm Hg, and/or a diastolic pressure >90 mm Hg or both. Pre-hypertension is defined as systolic blood pressure between 115 and 140 mm Hg, and/or a diastolic pressure between 80 and 90 mm Hg.

Obesity is a state of excess adipose tissue mass. Although not a direct measure of adiposity, the most widely used method to gauge obesity is the body mass index (BMI), which is equal to weight/height$^2$ (in kg/m$^2$) (See, e.g., Harrison's Principles of Experimental Medicine, 15th Edition, McGraw-Hill, Inc., N.Y.—hereinafter "Harrison's"). Based on data of substantial morbidity, a BMI of 30 is most commonly used as a threshold for obesity in both men and women. A BMI between 25 and 30 should be viewed as medically significant and worthy of therapeutic intervention, especially in the presence of risk factors that are influenced by adiposity, such as hypertension and glucose intolerance. Although often viewed as equivalent to increased body weight, this need not be the case. Lean but very muscular individuals may be overweight by arbitrary standards without having increased adiposity. Other approaches to quantifying obesity include anthropometry (skin-fold thickness), densitometry (underwater weighing), computed tomography (CT) or magnetic resonance imaging (MRI), and/or electrical impedance.

Diabetes mellitus is established in a human subject with a fasting plasma glucose level of 125 mg/dL or higher.

An elevated level(s) of a marker of systemic inflammation is a level that is above the average for a healthy human subject population (i.e., human subjects who have no signs and symptoms of disease). When the marker of systemic inflammation is CRP, a CRP level of ≥1 is considered an elevated level.

Therapies for reducing the risk of a future cardiovascular event include but are not limited to diet and/or exercise and/or therapies with: anti-lipemic agents, anti-inflammatory agents, antithrombotic agents, fibrinolytic agents, anti-platelet agents, direct thrombin inhibitors, glycoprotein IIb/IIIa receptor inhibitors, agents that bind to cellular adhesion molecules and inhibit the ability of white blood cells to attach to such molecules (e.g. anti-cellular adhesion molecule antibodies), alpha-adrenergic blockers, beta-adrenergic blockers, cyclooxygenase-2 inhibitors, angiotensin system inhibitor, anti-arrhythmics, calcium channel blockers, diuretics, inotropic agents, vasodilators, vasopressors, thiazolidinediones, cannabinoid-1 receptor blockers and/or any combinations thereof.

Anti-lipemic agents are agents that reduce total cholesterol, reduce LDLC, reduce triglycerides, and/or increase HDLC. Anti-lipemic agents include statins and non-statin anti-lipemic agents, and/or combinations thereof. Statins are a class of medications that have been shown to be effective in lowering human total cholesterol, LDLC and triglyceride levels. Statins act at the step of cholesterol synthesis. By reducing the amount of cholesterol synthesized by the cell, through inhibition of the HMG-CoA reductase gene, statins initiate a cycle of events that culminates in the increase of LDLC uptake by liver cells. As LDLC uptake is increased, total cholesterol and LDLC levels in the blood decrease. Lower blood levels of both factors are associated with lower risk of atherosclerosis and heart disease, and the statins are widely used to reduce atherosclerotic morbidity and mortality.

Examples of statins include, but are not limited to, simvastatin (Zocor), lovastatin (Mevacor), pravastatin (Pravachol), fluvastatin (Lescol), atorvastatin (Lipitor), cerivastatin (Baycol), rosuvastatin (Crestor), pitivastatin and numerous others.

Non-statin anti-lipemic agents include but are not limited to fibric acid derivatives (fibrates), bile acid sequestrants or resins, nicotinic acid agents, cholesterol absorption inhibitors, acyl-coenzyme A: cholesterol acyl transferase (ACAT) inhibitors, cholesteryl ester transfer protein (CETP) inhibitors, LDL receptor antagonists, farnesoid X receptor (FXR) antagonists, sterol regulatory binding protein cleavage activating protein (SCAP) activators, microsomal triglyceride transfer protein (MTP) inhibitors, squalene synthase inhibitors, and peroxisome proliferation activated receptor (PPAR) agonists.

Examples of fibric acid derivatives include but are not limited to gemfibrozil (Lopid), fenofibrate (Tricor), clofibrate (Atromid) and bezafibrate.

Examples of bile acid sequestrants or resins include but are not limited to colesevelam (WelChol), cholestyramine (Questran or Prevalite) and colestipol (Colestid), DMD-504, GT-102279, HBS-107 and S-8921.

Examples of nicotinic acid agents include but are not limited to niacin and probucol.

Examples of cholesterol absorption inhibitors include but are not limited to ezetimibe (Zetia).

Examples of ACAT inhibitors include but are not limited to Avasimibe, CI-976 (Parke Davis), CP-113818 (Pfizer), PD-138142-15 (Parke Davis), F1394, and numerous others described in U.S. Pat. Nos. 6,204,278, 6,165,984, 6,127,403, 6,063,806, 6,040,339, 5,880,147, 5,621,010, 5,597,835, 5,576,335, 5,321,031, 5,238,935, 5,180,717, 5,149,709, and 5,124,337.

Examples of CETP inhibitors include but are not limited to Torcetrapib, CP-529414, CETi-1, JTT-705, and numerous others described in U.S. Pat. Nos. 6,727,277, 6,723,753, 6,723,752, 6,710,089, 6,699,898, 6,696,472, 6,696,435, 6,683,099, 6,677,382, 6,677,380, 6,677,379, 6,677,375, 6,677,353, 6,677,341, 6,605,624, 6,586,448, 6,521,607, 6,482,862, 6,479,552, 6,476,075, 6,476,057, 6,462,092, 6,458,852, 6,458,851, 6,458,850, 6,458,849, 6,458,803, 6,455,519, 6,451,830, 6,451,823, 6,448,295, 5,512,548.

One example of an FXR antagonist is Guggulsterone. One example of a SCAP activator is GW532 (GlaxoSmithKline).

Examples of MTP inhibitors include but are not limited to Implitapide and R-103757.

Examples of squalene synthase inhibitors include but are not limited to zaragozic acids.

Examples of PPAR agonists include but are not limited to GW-409544, GW-501516, and LY-510929.

The invention involves identifying polymorphisms in the Apo(a) gene. Polymorphisms are allelic variants that occur in a population. The polymorphism can be a single nucleotide difference present at a locus, or can be an insertion or deletion of one or a few nucleotides at a position of a gene. As such, a single nucleotide polymorphism (SNP) is characterized by the presence in a population of one or two, three or four nucleotides (i.e., adenine, cytosine, guanine or thymine), typically less than all four nucleotides, at a particular locus in a genome such as the human genome.

Those skilled in the art will readily recognize that nucleic acid molecules may be double-stranded molecules and that reference to a particular site on one strand refers, as well, to the corresponding site on a complementary strand. In defining a SNP position, SNP allele, or nucleotide sequence, reference to an adenine, a thymine (uridine), a cytosine, or a guanine at a particular site on one strand of a nucleic acid molecule also defines the thymine (uridine), adenine, guanine, or cytosine (respectively) at the corresponding site on a complementary strand of the nucleic acid molecule. Thus, reference may be made to either strand in order to refer to a particular SNP position, SNP allele, or nucleotide sequence. Probes and primers, may be designed to hybridize to either strand and SNP genotyping methods disclosed herein may generally target either strand.

Determining the identity of a nucleotide in the Apo(a) gene can be performed, for example, by incubating the nucleic acid sample with an oligonucleotide probe or primer that selectively hybridizes to or near, respectively, a nucleic acid molecule comprising the nucleotide and detecting selective hybridization of the primer or probe. Selective hybridization of a probe can be detected, for example, by detectably labeling the probe, and detecting the presence of the label using a blot type analysis such as Southern blot analysis. Selective hybridization of a primer can be detected, for example, by performing a primer extension reaction, and detecting a primer extension reaction product comprising the primer. If desired, the primer extension reaction can be performed as a polymerase chain reaction. The method can include identifying one or more nucleotides.

Many analytical procedures may be used to detect the presence or absence of variant nucleotides at the polymorphic positions of the invention. In general, the detection of allelic variation requires a mutation discrimination technique, optionally an amplification reaction and optionally a signal generation system. A number of mutation detection techniques, some based on the PCR may be used in combination with a number of signal generation systems. Many current methods for the detection of allelic variation are reviewed by Nollau et al., Clin. Chem. 43, 1114-1120, 1997; and in standard textbooks, for example "Laboratory Protocols for Mutation Detection", Ed. by U. Landegren, Oxford University Press, 1996 and "PCR", 2nd Edition by Newton & Graham, BIOS Scientific Publishers Limited, 1997. Apo (a) gene SNP detection and genotyping methods and reagents are described in U.S. Patent Application Publication US2005/0272054A1 the entire contents of which are incorporated by reference herein.

To determine the percent identity of two nucleotide sequences or two amino acid sequences of two molecules that share sequence homology, the sequences are aligned for optimal comparison purposes (e.g., gaps can be introduced in one or both of a first and a second nucleic acid or amino acid sequence for optimal alignment and non-homologous sequences can be disregarded for comparison purposes). In some embodiments, at least 30%, 40%, 50%, 60%, 70%, 80%, or 90% or more of the length of a reference sequence is aligned for comparison purposes. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein, amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. (Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje; G., Academic Press, 1987; and Sequence Analysis Primer, Gribskov, M. and Devereux, J., eds., M Stockton Press, New York, 1991). In some embodiments, the percent identity between two amino acid sequences is determined using the Needleman and Wunsch algorithm (J. Mol. Biol. (48):444-453 (1970))

In some embodiments, the percent identity between two nucleotide sequences is determined using the GAP program in the GCG software package (Devereux, J., et al., Nucleic Acids Res. 12(1):387 (1984)), using a NWSgapdna.CMP matrix and a gap weight of 40, 50, 60, 70, or 80 and a length weight of 1, 2, 3, 4, 5, or 6. In other embodiments, the percent identity between two amino acid or nucleotide sequences is determined using the algorithm of E. Myers and W. Miller (CABIOS, 4:11-17 (1989) which has been incorporated into the ALIGN program (version 2.0), using a PAM120 weight residue table, a gap length penalty of 12, and a gap penalty of 4.

For analyzing SNPs, it may be appropriate to use oligonucleotides specific for alternative SNP alleles. Such oligonucleotides which detect single nucleotide variations in target sequences may be referred to by such terms as "allele-specific oligonucleotides", "allele-specific probes", or "allele-specific primers". The design and use of allele-specific probes for analyzing polymorphisms is described in, e.g., Mutation Detection A Practical Approach, ed. Cotton et al. Oxford University Press, 1998; Saiki et al., Nature 324, 163-166 (1986); Dattagupta, EP235,726; and Saiki, WO 89/11548.

While the design of each allele-specific primer or probe depends on variables such as the precise composition of the nucleotide sequences flanking a SNP position in a target nucleic acid molecule, and the length of the primer or probe, another factor in the use of primers and probes is the stringency of the condition under which the hybridization between the probe or primer and the target sequence is performed. Higher stringency conditions utilize buffers with lower ionic strength and/or a higher reaction temperature, and tend to require a more perfect match between probe/primer and a target sequence in order to form a stable duplex. If the stringency is too high, however, hybridization may not occur at all. In contrast, lower stringency conditions utilize buffers with higher ionic strength and/or a lower reaction temperature, and permit the formation of stable duplexes with more mismatched bases between a probe/primer and a target sequence. By way of example and not limitation, exemplary conditions for high stringency hybridization conditions using an allele-specific probe rate as follows: Prehybridization with a solution containing 5× standard saline phosphate-EDTA (SSPE), 0.5% $NaDodSO_4$ (SDS) at 55° C., and incubating probe with target nucleic acid molecules in the same solution at the same temperature, followed by washing with a solution containing 2×SSPE, and 0.1% SDS at 55° C. or room temperature.

Moderate stringency hybridization conditions may be used for allele-specific primer extension reactions with a solution containing, e.g., about 50 mM KCl at about 46° C. Alternatively, the reaction may be carried out at an elevated temperature such as 60° C. In another embodiment, a moderately stringent hybridization condition suitable for oligonucleotide ligation assay (OLA) reactions wherein two probes are ligated if they are completely complementary to the target sequence may utilize a solution of about 100 mM KCl at a temperature of 46° C.

In a hybridization-based assay, allele-specific probes can be designed that hybridize to a segment of target DNA from one individual but do not hybridize to the corresponding segment from another individual due to the presence of different polymorphic forms (e.g., alternative SNP alleles/nucleotides) in the respective DNA segments from the two individuals. Hybridization conditions should be sufficiently stringent that there is a significant detectable difference in hybridization intensity between alleles, and preferably an essentially binary response, whereby a probe hybridizes to only one of the alleles or significantly more strongly to one allele. While a probe may be designed to hybridize to a target sequence that contains a SNP site such that the SNP site aligns anywhere along the sequence of the probe, the probe is preferably designed to hybridize to a segment of the target sequence such that the SNP site aligns with a central position of the probe (e.g., a position within the probe that is at least three nucleotides from either end of the probe).

This design of probe generally achieves good discrimination in hybridization between different allelic forms.

The nucleotide sequence (polynucleotide or oligonucleotide) can be RNA or can be DNA, which can be a gene or a portion thereof, a cDNA, a synthetic polydeoxyribonucleic acid sequence, or the like, and can be single stranded or double stranded, as well as a DNA/RNA hybrid. In various embodiments, a polynucleotide, including an oligonucleotide (e.g., a probe or a primer) can contain nucleoside or nucleotide analogs, or a backbone bond other than a phosphodiester bond. In general, the nucleotides comprising a polynucleotide are naturally occurring deoxyribonucleotides, such as adenine, cytosine, guanine or thymine linked to 2'-deoxyribose, or ribonucleotides such as adenine, cytosine, guanine or uracil linked to ribose. However, a polynucleotide or oligonucleotide also can contain nucleotide analogs, including non-naturally occurring synthetic nucleotides or modified naturally occurring nucleotides. Such nucleotide analogs are well known in the art and commercially available, as are polynucleotides containing such nucleotide analogs (Lin et al., Nucl. Acids Res. 22: 5220-5234(1994); Jellinek et al., Biochemistry 34: 11363-11372 (1995); Pagratis et al., Nature Biotechnol. 15:68-73 (1997), each of which is incorporated herein by reference).

The covalent bond linking the nucleotides of a polynucleotide generally is a phosphodiester bond. However, the covalent bond also can be any of numerous other bonds, including a thiodiester bond, a phosphorothioate bond, a peptide-like bond or any other bond known to those in the art as useful for linking nucleotides to produce synthetic polynucleotides (see, for example, Tam et al., Nucl. Acids Res. 22: 977-986 (1994); Ecker and Crooke, BioTechnology 13:351360 (1995), each of which is incorporated herein by reference). The incorporation of non-naturally occurring nucleotide analogs or bonds linking the nucleotides or analogs can be particularly useful where the polynucleotide is to be exposed to an environment that can contain a nucleolytic activity, including, for example, a tissue culture medium or upon administration to a living subject, since the modified polynucleotides can be less susceptible to degradation.

A polynucleotide or oligonucleotide comprising naturally occurring nucleotides and phosphodiester bonds can be chemically synthesized or can be produced using recombinant DNA methods, using an appropriate polynucleotide as a template. In comparison, a polynucleotide or oligonucleotide comprising nucleotide analogs or covalent bonds other than phosphodiester bonds generally are chemically synthesized, although an enzyme such as T7 polymerase can incorporate certain types of nucleotide analogs into a polynucleotide and, therefore, can be used to produce such a polynucleotide recombinantly from an appropriate template (Jellinek et al., supra, 1995). Thus, the term polynucleotide as used herein includes naturally occurring nucleic acid molecules, which can be isolated from a cell, as well as synthetic molecules, which can be prepared, for example, by methods of chemical synthesis or by enzymatic methods such as by the polymerase chain reaction (PCR).

The test sample of nucleic acid is conveniently a sample of blood, bronchoalveolar lavage fluid, sputum, or other body fluid or tissue obtained from a subject (e.g., human). It will be appreciated that the test sample may equally be a nucleic acid sequence corresponding to the sequence in the test sample, that is to say that all or a part of the region in the sample nucleic acid may firstly be amplified using any convenient technique e.g. PCR, before analysis of allelic variation.

In various embodiments, it can be useful to detectably label a polynucleotide or oligonucleotide. Detectable labeling of a polynucleotide or oligonucleotide is well known in the art. Particular non-limiting examples of detectable labels include chemiluminescent labels, radiolabels, enzymes, haptens, or even unique oligonucleotide sequences.

A method of identifying a polymorphism also can be performed using a specific binding pair member. As used herein, the term "specific binding pair member" refers to a molecule that specifically binds or selectively hybridizes to another member of a specific binding pair. Specific binding pair members include, for example, probes, primers, polynucleotides, antibodies, etc. For example, a specific binding pair member includes a primer or a probe that selectively hybridizes to a target polynucleotide that includes a polymorphism loci, or that hybridizes to an amplification product generated using the target polynucleotide as a template.

As used herein, the term "specific interaction," or "specifically binds" or the like means that two molecules form a complex that is relatively stable under physiologic conditions. The term is used herein in reference to various interactions, including, for example, the interaction of an antibody that binds a polynucleotide that includes a polymorphism site; or the interaction of an antibody that binds a polypeptide that includes an amino acid that is encoded by a codon that includes a polymorphism site.

According to methods of the invention, an antibody can selectively bind to a polypeptide that includes a particular amino acid encoded by a codon that includes a polymorphism site. Alternatively, an antibody may preferentially bind a particular modified nucleotide that is incorporated into a polymorphism site for only certain nucleotide occurrences at the polymorphism site, for example using a primer extension assay.

A specific interaction generally is stable under physiological conditions, including, for example, conditions that occur in a living individual such as a human or other vertebrate or invertebrate, as well as conditions that occur in a cell culture such as used for maintaining mammalian cells or cells from another vertebrate organism or an invertebrate organism. Methods for determining whether two molecules interact specifically are well known and include, for example, equilibrium dialysis, surface plasmon resonance, and the like.

Numerous methods are known in the art for determining the nucleotide occurrence for a particular polymorphism in a sample. Such methods can utilize one or more oligonucleotide probes or primers, including, for example, an amplification primer pair, that selectively hybridize to a target polynucleotide, which contains one or more polymorphisms in the Apo(a) gene.

An allele specific primer is used, generally together with a constant primer, in an amplification reaction such as a PCR reaction, which provides the discrimination between alleles through selective amplification of one allele at a particular sequence position e.g. as used for ARMS™ assays. The allele specific primer is preferably 17-50 nucleotides, more preferably about 17-35 nucleotides, more preferably about 17-30 nucleotides.

An allele specific primer preferably corresponds exactly with the allele to be detected but derivatives thereof are also contemplated wherein about 6-8 of the nucleotides at the 3' terminus correspond with the allele to be detected and wherein up to 10, such as up to 8, 6, 4, 2, or 1 of the remaining nucleotides may be varied without significantly affecting the properties of the primer. Primers may be manufactured using any convenient method of synthesis. Examples of such methods may be found in standard textbooks, for example "Protocols for Oligonucleotides and Analogues; Synthesis and Properties," Methods in Molecular Biology Series; Volume 20; Ed. Sudhir Agrawal, Humana ISBN: 0-89603-247-7; 1993; 1st Edition. If required the primer(s) may be labeled to facilitate detection.

An allele-specific oligonucleotide probe may be used to detect the Apo(a) gene polymorphism at the position defined herein. The design of such probes will be apparent to the molecular biologist of ordinary skill in the art. Such probes are of any convenient length such as up to 50 bases, up to 40 bases, more conveniently up to 30 bases in length, such as for example 8-25 or 8-15 bases in length. In general such probes will comprise base sequences entirely complementary to the corresponding wild type or variant locus in the gene. However, if required one or more mismatches may be introduced, provided that the discriminatory power of the oligonucleotide probe is not unduly affected. The probes of the invention may carry one or more labels to facilitate detection.

Oligonucleotide probes useful in practicing a method of the invention can include, for example, an oligonucleotide that is complementary to and spans a portion of the target polynucleotide, including the position of the polymorphism, wherein the presence of a specific nucleotide at the position is detected by the presence or absence of selective hybridization of the probe. Such a method can further include contacting the target polynucleotide and hybridized oligonucleotide with an endonuclease, and detecting the presence or absence of a cleavage product of the probe, depending on whether the nucleotide occurrence at the polymorphism site is complementary to the corresponding nucleotide of the probe.

An oligonucleotide ligation assay also can be used to identify a nucleotide occurrence at a polymorphic position, wherein a pair of probes that selectively hybridize upstream and adjacent to and downstream and adjacent to the site of the polymorphism, and wherein one of the probes includes a terminal nucleotide complementary to a nucleotide occurrence of the polymorphism. Where the terminal nucleotide of the probe is complementary to the nucleotide occurrence, selective hybridization includes the terminal nucleotide such that, in the presence of a ligase, the upstream and downstream oligonucleotides are ligated. As such, the presence or absence of a ligation product is indicative of the nucleotide occurrence at the site of polymorphism.

An oligonucleotide also can be useful as a primer, for example, for a primer extension reaction, wherein the product (or absence of a product) of the extension reaction is indicative of the nucleotide occurrence. In addition, a primer pair useful for amplifying a portion of the target polynucleotide including the SNP site can be useful, wherein the amplification product is examined to determine the nucleotide occurrence at the polymorphism site. Particularly useful methods include those that are readily adaptable to a high throughput format, to a multiplex format, or to both. The primer extension or amplification product can be detected directly or indirectly and/or can be sequenced using various methods known in the art. Amplification products which span a polymorphism locus can be sequenced using traditional sequence methodologies (e.g., the "dideoxy-mediated chain termination method," also known as the "Sanger Method" (Sanger, F., et al., J. Molec. Biol. 94: 441 (1975); Prober et al. Science 238: 336-340 (1987)) and the "chemical degradation method" also known as the "Maxam-Gilbert method" (Maxam, A. M., et al., Proc. Natl. Acad. Sci. (U.S.A) 74: 560 (1977)), both references herein incorporated by reference) to determine the nucleotide occurrence at the SNP loci.

Methods that can determine the identity of a nucleotide in the Apo(a) gene include using a "microsequencing" method. Microsequencing methods determine the identity of only a single nucleotide at a "predetermined" site. Such methods have particular utility in determining the presence and identity of polymorphisms in a target polynucleotide.

Such microsequencing methods, as well as other methods for determining the nucleotide occurrence at a polymorphism loci are discussed in Boyce-Jacino, et al., U.S. Pat. No. 6,294,336, incorporated herein by reference.

Microsequencing methods include the Genetic Bit Analysis method disclosed by Goelet, P. et al. (WO 92/15712, herein incorporated by reference). Additional, primer-guided, nucleotide incorporation procedures for assaying polymorphic sites in DNA have also been described (Komher, J. S. et al, Nucl. Acids. Res. 17: 7779-7784 (1989); Sokolov, B. P., Nucl. Acids Res. 18: 3671 (1990); Syvanen, A.-C., et al., Genomics 8: 684-692 (1990); Kuppuswamy, M. N. et al., Proc. Natl. Acad. Sci. (U.S.A) 88: 1143-1147 (1991); Prezant, T. R. et al., Hum. Mutat. 1: 159-164 (1992); Ugozzoli, L. et al., GATA 9: 107-112 (1992); Nyren, P. et al., Anal. Biochem. 208: 171-175 (1993); and Wallace, WO89/10414). These methods differ from Genetic Bit. Analysis in that they all rely on the incorporation of labeled deoxynucleotides to discriminate between bases at a polymorphic site. In such a format, since the signal is proportional to the number of deoxynucleotides incorporated, polymorphisms that occur in runs of the same nucleotide can result in signals that are proportional to the length of the run (Syvanen, A.-C., et al. Amer. J. Hum. Genet. 52: 46-59 (1993)).

Alternative microsequencing methods have been provided by Mundy, C. R. (U.S. Pat. No. 4,656,127) and Cohen, D. et al. (French Patent 2,650,840; PCT Appln. No. WO91/02087) which discusses a solution-based method for determining the identity of the nucleotide of a polymorphic site. As in the Mundy method of U.S. Pat. No. 4,656,127, a primer is employed that is complementary to allelic sequences immediately 3'-to a polymorphic site.

In response to the difficulties encountered in employing gel electrophoresis to analyze sequences, alternative methods for microsequencing have been developed. Macevicz (U.S. Pat. No. 5,002,867), for example, describes a method for determining nucleic acid sequence via hybridization with multiple mixtures of oligonucleotide probes. In accordance with such method, the sequence of a target polynucleotide is determined by permitting the target to sequentially hybridize with sets of probes having an invariant nucleotide at one position, and a variant nucleotide at other positions. The Macevicz method determines the nucleotide sequence of the target by hybridizing the target with a set of probes, and then determining the number of sites that at least one member of the set is capable of hybridizing to the target (i.e., the number of "matches"). This procedure is repeated until each member of a sets of probes has been tested.

Boyce-Jacino, et al., U.S. Pat. No. 6,294,336 provides a solid phase sequencing method for determining the sequence of nucleic acid molecules (either DNA or RNA) by utilizing a primer that selectively binds a polynucleotide target at a site wherein the SNP is the most 3' nucleotide selectively bound to the target.

Accordingly, using the methods described above, the acetylsalicylic acid response-related haplotype allele or the nucleotide occurrence of the acetylsalicylic acid response-related SNP can be identified using an amplification reaction, a primer extension reaction, or an immunoassay. The acetylsalicylic acid response-related haplotype allele or the nucleotide occurrence of the acetylsalicylic acid response related SNP can also be identified by contacting polynucleotides in the sample or polynucleotides derived from the sample, with a specific binding pair member that selectively hybridizes to a polynucleotide region comprising the acetylsalicylic acid response related SNP, under conditions wherein the binding pair member specifically binds at or near the acetylsalicylic acid response-related SNP. The specific binding pair member can be an antibody or a polynucleotide.

Antibodies that are used in the methods of the invention include antibodies that specifically bind polynucleotides that encompass polymorphism in the Apo(a) gene. In addition, antibodies bind polypeptides that include an amino acid encoded by a codon that includes the polymorphism. These antibodies bind to a polypeptide that includes an amino acid that is encoded in part by the polymorphism. Other methods that may be used include genotyping methods that incorporate a modified nucleotide that is subsequently recognized by an antibody such as, for example, Illumina's Infinium II Assay.

The antibodies specifically bind a polypeptide that includes a first amino acid encoded by a codon that includes the polymorphism loci, but do not bind, or bind more weakly to a polypeptide that includes a second amino acid encoded by a codon that includes a different nucleotide occurrence in the Apo(a) gene.

Antibodies include, but are not limited to, polyclonal, monoclonal, multispecific, human, humanized or chimeric antibodies, single chain antibodies, Fab fragments, F (ab') fragments, fragments produced by a Fab expression library, anti-idiotypic (anti-Id) antibodies (including, e.g., anti-Id antibodies to antibodies of the invention), and epitope-binding fragments of any of the above. The immunoglobulin molecules of the invention can be of any type (e.g., IgG, IgE, IgM, IgD, IgA and IgY), class (e.g., IgG1, IgG2, IgG3, IgG4, IgA1 and IgA2) or subclass of immunoglobulin molecule.

Antibodies include antibody fragments that include, but are not limited to, Fab, Fab' and F (ab') 2, Fd, single-chain Fvs (scFv), single-chain antibodies, disulfide-linked Fvs (sdFv) and fragments comprising either a VL or VH domain. Antigen-binding antibody fragments, including single-chain antibodies, may comprise the variable region(s) alone or in combination with the entirety or a portion of the following: hinge region, CH1, CH2, and CH3 domains. Also included are antigen-binding fragments also comprising any combination of variable region(s) with a hinge region, CH1, CH2, and CH3 domains. The antibodies may be from any animal origin including birds and mammals. Preferably, the antibodies are human, murine (e.g., mouse and rat), donkey, ship rabbit, goat, guinea pig, camel, horse, or chicken. The antibodies may be monospecific, bispecific, trispecific or of greater multispecificity.

The antibodies may be generated by any suitable method known in the art. Polyclonal antibodies to an antigen-of-interest can be produced by various procedures well known in the art. For example, a polypeptide of the invention can be administered to various host animals including, but not limited to, rabbits, mice, rats, etc., to induce the production of sera containing polyclonal antibodies specific for the antigen. Various adjuvants may be used to increase the immunological response, depending on the host species, and include but are not limited to, Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *Corynebacterium parvum*. Such adjuvants are also well known in the art.

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example; in Harlow et al., Antibodies: A Laboratory Manual, (Cold Spring Harbor Laboratory Press, 2nd ed. 1988); Hammerling, et al., in: Monoclonal Antibodies and T-Cell Hybridomas 563-681 (Elsevier, N.Y., 1981) (said references incorporated by reference in their entireties). The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced.

After all the relevant phenotypic and genotypic information has been obtained, statistical analyses are carried out to determine if there is any significant correlation between the presence of an allele or a genotype with the phenotypic characteristics of an individual. Allele frequencies, Hardy-Weinberg equilibrium statistics, and linkage disequilibrium (LD) between SNPs can be calculated. Haplotypes can then be calculated using, for example, an EM algorithm (Excoffier and Slatkin, Mol Biol Evol. 1995 September; 12 (S): 921-7). There are also other methods for inferring haplotypes that do not use the EM approach to estimate frequency. These methods are based on reconstructions of evolutionary history, including recombination and the coalescent, and are represented in, for example, the program PHASE (Stephens, M., Smith, N., and Donnelly, P. *American Journal of Human Genetics*, 68, 978-989, 2001). In addition to various parameters such as linkage disequilibrium coefficients, allele frequencies, chi square statistics and other population genetic parameters such as Panmitic indices can be calculated to control for ethnic, ancestral or other systematic variation between the case and control groups.

Preferably, data inspection and cleaning are first performed before carrying out statistical tests for genetic association. Epidemiological and clinical data of the samples can be summarized by descriptive statistics with tables and graphs. Data validation is preferably performed to check for data completion, inconsistent entries, and outliers. Chi-squared tests and t-tests (Wilcoxon rank-sum tests if distributions are not normal) may then be used to check for significant differences between cases and controls for discrete and continuous variables, respectively. To ensure genotyping quality, Hardy-Weinberg disequilibrium tests can be performed on cases and controls separately. Significant deviation from Hardy-Weinberg equilibrium (HWE) in both cases and controls for individual markers can be indicative of genotyping errors. If HWE is violated in a majority of markers, it is indicative of population substructure that should be further investigated. Moreover, Hardy-Weinberg disequilibrium in cases only can indicate genetic association of the markers with the disease (Genetic Data Analysis, Weir B., Sinauer (1990)).

To test whether an allele of a single SNP is associated with the case or control status of a phenotypic trait, one skilled in the art can compare allele frequencies in cases and controls. Standard chi-squared tests and Fisher exact tests can be carried out on a 2×2 table (2 SNP alleles X2 outcomes in the categorical trait of interest). To test whether genotypes of a SNP are associated, chi-squared tests can be carried out on a 3×2 table (3 genotypes X2 outcomes). Score tests are also carried out for genotypic association to contrast the three genotypic frequencies (major homozygotes, heterozygotes and minor homozygotes) in cases and controls, and to look for trends using 3 different modes of inheritance, namely dominant (with contrast coefficients 2, −1, −1), additive (with contrast coefficients 1, 0, −1) and recessive (with contrast coefficients 1, 1, −2). Odds ratios for minor versus major alleles, and odds ratios for heterozygote and homozygote variants versus the wild type genotypes are calculated with the desired confidence limits, usually 95%.

Polymorphisms with value for distinguishing the case matrix from the control, if any, can be presented in mathematical form describing any relationship and accompanied by association (test and effect) statistics. A statistical analysis result which shows an association of a polymorphism marker with an acetylsalicylic acid response with at least 80%, 85%, 90%, 95%, or 99%, most preferably 95% confidence, or alternatively a probability of insignificance less than 0.05, may be used.

In a further aspect, the diagnostic methods of the invention are used to assess the pharmacogenetics of acetylsalicylic acid treatment to reduce the risk of a future cardiovascular event. Individuals who carry particular allelic variants of the Apo(a) gene may therefore display altered abilities to react to different agents or therapies such as acetylsalicylic acid treatment. This may have a direct effect on the response of an individual to drug therapy. The diagnostic methods of the invention may be useful both to predict the clinical response to acetylsalicylic acid treatment and to determine therapeutic dose.

Thus, the present invention provides methods for selecting or formulating a treatment regimen (e.g., methods for determining whether or not to administer acetylsalicylic acid to an individual methods for selecting a particular treatment regimen such as dosage and frequency of administration of acetylsalicylic acid, or selecting an alternative antithrombotic treatment (i.e., other than acetylsalicylic acid) to individuals who are predicted to be unlikely to respond to acetylsalicylic acid treatment, and methods for determining the likelihood of experiencing toxicity or other undesirable side effects from acetylsalicylic acid treatment, etc.). The present invention also provides methods for selecting individuals to whom acetylsalicylic acid treatment or other treatment will be administered based on the individual's genotype, and methods for selecting individuals for a clinical trial of a acetylsalicylic acid treatment or other therapeutic agent based on the genotypes of the individuals (e.g., selecting individuals to participate in the trial who are most likely to respond positively to the acetylsalicylic acid treatment).

The SNPs of the present invention can also be used to identify novel therapeutic targets. For example, genes containing the polymorphism or their products, as well as genes or their products that are directly or indirectly regulated by or interacting with these polymorphisms or their products, can be targeted for the development of therapeutics. The methods of the invention are used in the development of new drug therapies which selectively target one or more variants of the Apo(a) gene. Identification of a link between a particular variant and predisposition to disease development or response to drug treatment may have a significant impact on the design of new drugs. Drugs may be designed to regulate the biological activity of variants implicated in disease processes. The therapeutics may be composed of, for example, small molecules, proteins, protein fragments or peptides, antibodies, nucleic acids, or their derivatives or mimetics which modulate the functions or levels of the target genes or gene products.

According to another aspect of the invention, there is provided a diagnostic kit comprising an allele specific nucleotide probe of the invention and/or an allele-specific primer of the invention. The diagnostic kits may comprise appropriate packaging and instructions for use in the methods of the invention. Such kits may further comprise appropriate buffer(s) and polymerase(s) such as thermostable polymerases, for example taq polymerase.

In another aspect of the invention, the single nucleotide polymorphisms of this invention may be used as genetic markers in linkage studies. This particularly applies to the polymorphisms of relatively high frequency. Low frequency polymorphisms may be particularly useful for haplotyping as described below. A haplotype is a set of alleles found at linked polymorphic sites (such as within a gene) on a single (paternal or maternal) chromosome. If recombination within the gene is random, there may be as many as $2^n$ haplotypes, where 2 is the number of alleles at each SNP and n is the number of SNPs. One approach to identifying mutations or polymorphisms which are correlated with clinical response is to carry out an association study using all the haplotypes that can be identified in the population of interest. The frequency of each haplotype is limited by the frequency of its rarest allele, so that SNPs with low frequency alleles are particularly useful as markers of low frequency haplotypes. As particular mutations or polymorphisms associated with certain clinical features are likely to be of low frequency within the population, low frequency SNPs may be particularly useful in identifying these mutations.

According to another aspect of the present invention there is provided a method of treatment. The method of treatment comprises selecting a human subject on the basis that the human subject has an Apo(a) polymorphism characterized by cytosine or guanine at chromosome 6:160880877 (March 2006 assembly—NCBI build 36.1; rs3798220 dbSNP @ NCBI) and administering to the subject a particular dose of acetylsalicylic acid or an agent other than acetylsalicylic acid (e.g. an antithrombotic agent such as a thienopyridine or a thienopyridine derivative) for reducing the risk of an adverse cardiovascular event because the subject has the polymorphism.

Preferably determination of the status of the human subject is clinically useful. Examples of clinical usefulness include deciding which antithrombotic drug or drugs to administer and/or in deciding on the effective amount of the drug or drugs. Examples of antithrombotic agents are provided above.

The invention relates to methods for evaluating a human subject's responsiveness to acetylsalicylic treatment to reduce the risk of a future cardiovascular event. The methods of the invention are based, in part, determining the identity of a nucleotide at position 6:160880877 (March 2006 assembly—NCBI build 36.1; rs3798220 dbSNP @ NCBI) of a subject's Apo(a) gene that, alone or in combination, allow an inference to be drawn as to the subject's acetylsalicylic response. The acetylsalicylic response can be a reduction in the risk of a cardiovascular disorder. As such, the compositions and methods of the invention are useful, for example, for identifying individuals or patients who are more or less likely to respond to acetylsalicylic acid treatment or to treatment with an antithrombotic agent other than acetylsalicylic acid. The compositions and methods of the invention are also useful for predicting or determining that an individual or patient may require an altered dose of acetylsalicylic acid or of an antithrombotic agent other than acetylsalicylic acid to reduce the risk of a cardiovascular disorder.

According to another aspect of the invention, an assay is provided. The assay involves screening for an agent that binds preferentially to Apo(a) protein (e.g., isolated Apo(a) protein) or to Lp(a) encoded by an Apo(a) gene having cytosine or guanine at the position chromosome 6:160880877 (March 2006 assembly—NCBI build 36.1; rs3798220 dbSNP @ NCBI.

The invention also provides another assay. The assay involves screening for an agent that binds preferentially to Apo(a) protein (e.g., isolated Apo(a) protein) or to Lp(a) encoded by an Apo(a) gene having thymine or adenine at the position chromosome 6:160880877 (March 2006 assembly—NCBI build 36.1; rs3798220 dbSNP @ NCBI.

The screening assays can be used to select among antithrombotic agents those which preferentially bind to a polymorphism. Rational drug design may be carried out through altering or making versions of existing antithrombotic agents and then testing the relative ability of such versions to bind preferentially one or another polymorphism in the screening assay of the invention. Likewise chemical libraries of existing or novel agents may be screened for such binding.

The skilled artisan is familiar with screening methodologies. Screening assays include assays that measure the ability of an agent to bind a Lp(a) protein. For example, screening for an agent that binds preferentially to a polymorphism of a Lp(a) comprises contacting the agent with a polymorphism of a Lp(a), determining the binding of the agent to the polymorphism of a Lp(a), comparing the binding of the agent to the polymorphism of a Lp(a) not containing the polymorphism, wherein an increased binding of the agent to a polymorphism of a Lp(a) compared to the binding of the agent to the polymorphism of a Lp(a) not containing the polymorphism indicates that the agent is an antithrombotic agent with improved efficacy in the polymorphism of the a Lp(a) and wherein a decreased binding of the agent to a polymorphism of a Lp(a) compared to the binding of the agent to the polymorphism of a Lp(a) not containing the polymorphism indicates that the agent is an antithrombotic agent with reduced efficacy for the polymorphism of the Lp(a). The skilled artisan is familiar with this and other screening methodologies including but not limited to direct binding assays, competitive binding assays, non-competitive binding assays, functional inhibition assays, high through-put screening assays and the like.

The invention is illustrated but not limited by reference to the following Examples.

EXAMPLES

Example 1

Lipoprotein(a) [Lp(a)] is a plasma fraction that consists of a single (Apo(a)) molecule covalently linked through a disulfide bond to a single apolipoprotein B-100 molecule together with cholesterol-rich lipid (1). While the biological functions of Lp(a) remain uncertain (2, 3), high levels of Lp(a) have been associated with increased cardiovascular (CV) risk, particularly when LDL-C is also elevated (4-6). The cholesterol-bearing aspects of Lp(a) have largely focused investigation of associated cardiovascular risk on lipid-based biology (7-11). However, apolipoprotein(a) is also highly homologous to plasminogen, and in spite of a lack of recognized proteolytic activity in apolipoprotein(a), this homology has focused alternative investigations of cardiovascular risk on roles of Lp(a) in hemostasis, platelet function, and thrombosis (12-18).

The apolipoprotein(a) locus is among the most polymorphic in the human genome. Apolipoprotcin(a) genetic variation has been associated with the wide range of Lp(a) levels and largely accounts for the heritability of Lp(a) (19-22). Most of the known variation that influences Lp(a) levels takes the form of between 3 and 40 repeats of the Kringle (Kr) IV type 2 domain located toward the amino terminus of the protein (1, 23). This high degree of Kr IV type 2 polymorphism had presented a challenge for measuring plasma Lp(a) levels until the recent development of assay reagents that recognize the single Kr V domain of apolipoprotein(a) and do not cross-react with the Kr IV type 2 repeats (24, 25). Other apolipoprotein(a) gene variants that have been associated with Lp(a) levels include single nucleotide polymorphisms (SNP) as well as insertion-deletion polymorphisms, notably of a pentanucleotide sequence, TTTTA, in the promoter (26-28). In addition, polymorphism of the apolipoprotein(a) locus appears to involve copy number variation (29).

Recently, the SNP rs3798220, encoding an isoleucine to methionine substitution in the plasminogen protease-like domain of apolipoprotein(a), has been suggested as a novel candidate for association with both Lp(a) levels and prevalent cardiovascular disease (Luke et al., submitted (30)). The genotype of this polymorphism was therefore determined among 26,274 initially healthy women from the Women's Health Study (WHS) who had been randomly allocated to low dose aspirin or placebo and then followed over a 10-year period for incident cardiovascular events (31). This setting afforded the opportunity for prospective assessment not only of rs3798220 association with Lp(a) levels and vascular risk, but also of an interaction between aspirin and genetic effects on risk. Although most of the study participants were Caucasian, there were sufficient numbers of non-Caucasian participants to address population-specific influences on associations between rs3798220 and Lp(a) levels, as have been found in previous comparisons of other apolipoprotein (a) variants among populations with different biogeographic ancestry (32-36).

Among 25,038 Caucasian participants in the WHS, the minor allele of rs3798220 in the apolipoprotein(a) gene was carried by 904 (3.6%) heterozygotes and 15 (0.06%) homozygotes for a minor allele frequency of 1.9%. These genotypes represent a borderline deviation from Hardy-Weinberg equilibrium (p=0.048) due to slight deficiency of heterozygotes and excess of homozygotes of the minor allele. Age, BMI, smoking rates, hormone replacement therapy use, and menopausal status as well as incidence of hypertension and diabetes were not different among the three genotypic classes (Table 1). However, median Lp(a) levels in heterozygous (79.3 mg/dL) and homozygous carriers of the minor allele (153.9 mg/dL) were respectively eight and 15 times higher than the Lp(a) levels in non-carriers (10.0 mg/dL, p<<0.001) (Table 1, FIG. 1A, FIG. 1B). This effect appeared to underlie modest but significant elevations of the related plasma fractions total cholesterol, LDL-C, and apolipoprotein B as judged by the elimination of significance after adjustment for Lp(a) levels. Other plasma biomarkers, including markers of inflammation and other lipid fractions, were not associated with rs3798220 genotype. Essentially identical results were found in analyses combining the heterozygotes with the homozygous carriers of the minor allele in comparisons of clinical characteristics with non-carriers (data not shown).

Figure 1B:
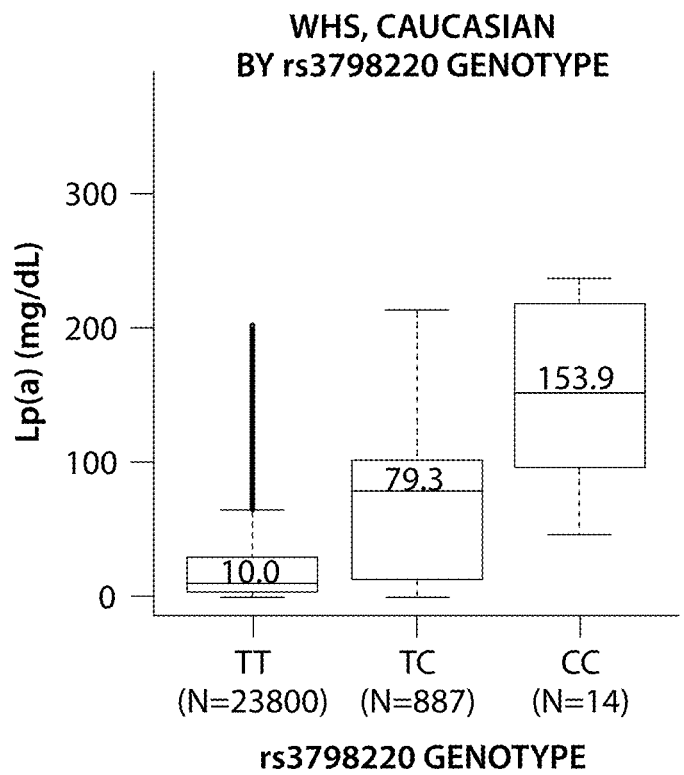
Figure 1C:
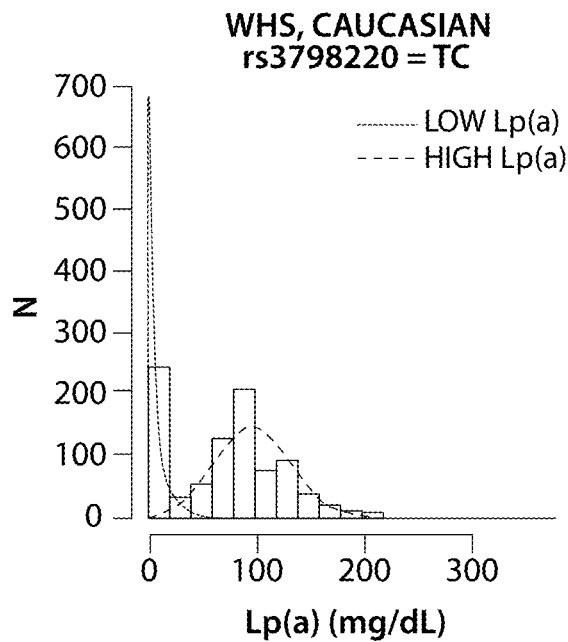
Figure 1D:
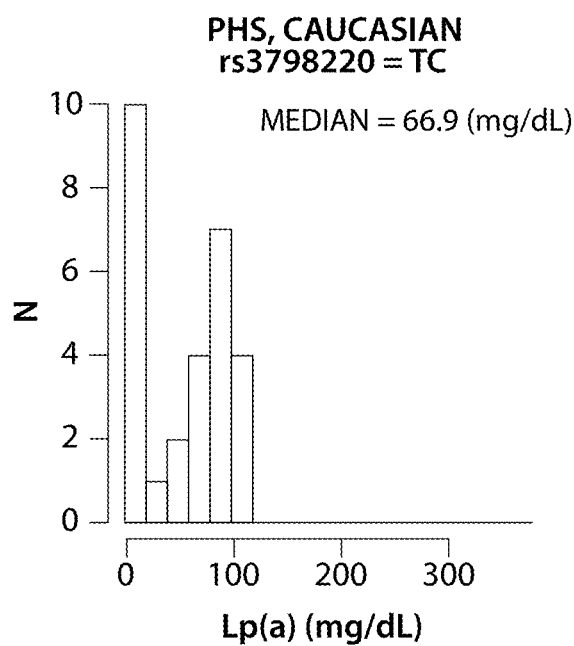

The distribution of Lp(a) levels among Caucasian heterozygotes was entirely different from that among non-carriers and had a fully bimodal pattern that allowed stratification of this subpopulation into one group with Lp(a) greater than 27.9 mg/dL (median 92.4 mg/dL, N=627) and a second group with Lp(a) less than 27.9 mg/dL (median 5.0 mg/dL, N=260) (FIGS. 1A-1C). All homozygous carriers of the minor allele had Lp(a) levels greater than 27.9 mg/dL, but there were too few individuals in this group to evaluate the shape of the Lp(a) distribution (FIG. 1B). The bimodal distribution of Lp(a) among rs3798220 heterozygotes was confirmed in a second unrelated population of 1058 Caucasian men from the Physicians' Health Study (PHS) where the minor allele frequency of rs3798220 was 1.8%, similar to its frequency in the Caucasian WHS women (FIG. 1D).

The bimodal nature of Lp(a) levels among Caucasian heterozygotes could not be explained by standard clinical characteristics. For example, there were no significant differences in the comparison of Caucasian heterozygous women with low or high Lp(a) in terms of age, BMI, smoking, diabetes, menopausal status, hypertension, family history of heart disease, or use of hormone replacement therapy. Similarly, HDL-C, apolipoprotein A1, triglycerides, C-reactive protein, soluble ICAM-I, fibrinogen, creatinine, homocysteine, and HbA1c were all comparable in the two subpopulations of the heterozygotes, and similar to the level among homozygotes for the major allele. Moreover, gross geographic assignment across the US did not suggest a regional basis for the bimodal Lp(a) levels. LDL-C, total cholesterol, and apolipoprotein B levels were significantly elevated in heterozygotes with high Lp(a) compared to heterozygotes with low Lp(a) (medians: LDL-C, 130.5 mg/dL v. 122.5 mg/dL; total cholesterol, 219.0 mg/dL v. 210.4 mg/dL; apolipoprotein B, 109.9 mg/dL v. 103.1 mg/dL; all p<0.01), but the differences were again not significant after adjustment by Lp(a). Thus, the higher levels of these lipids observed overall among heterozygotes can be explained by the increase in Lp(a). Bimodal distributions were not observed for any of these lipids among the Caucasian heterozygous WHS participants.

The single copy of the minor allele of rs3798220 in heterozygotes conferred an approximate 50% increase in the risk of a future vascular event among the 24,320 Caucasian study participants who collectively experienced 825 cases of a first-ever event of the total CVD composite endpoint during the 10-year follow-up period (Table 2; age adjusted HR 1.50, 95% CI:1.09-2.05, p=0.012). None of the events occurred among the 15 homozygous carriers of the minor allele consistent with the low incidence rate overall, and therefore these few individuals were excluded from the analysis of the risk of future incident disease. The magnitude of the effect of rs3798220 was similar for the specific endpoints of MI, ischemic stroke, and revascularization. Thus, for the more clinically relevant endpoint of major vascular events (non-fatal MI, non-fatal ischemic stroke, and cardiovascular death), the age-adjusted hazard ratio was 1.58 (95% CI: 1.07-2.33, p=0.021). These effects remained statistically significant after adjustment for traditional cardiovascular risk factors so that the fully adjusted hazard ratio for total vascular events was 1.50 (1.07-2.10, p=0.009), and the fully adjusted hazard ratio for major vascular events was 1.54 (CI:1.01-2.35, p=0.043). Almost all of the increased risk among heterozygotes was limited to those with elevated Lp(a) levels (Table 2). For example, for major cardiovascular events, the age-adjusted hazard ratio for the heterozygotes with high Lp(a) [1.78 (CI:1.26-2.51, p=0.001)] was greater and more significant than for all heterozygotes, while the hazard ratio for heterozygotes with low Lp(a) [0.84 (CI:0.84-1.77, p=0.65)] was less than and not statistically different from the risk among noncarriers (Table 2).

Figure 2A:
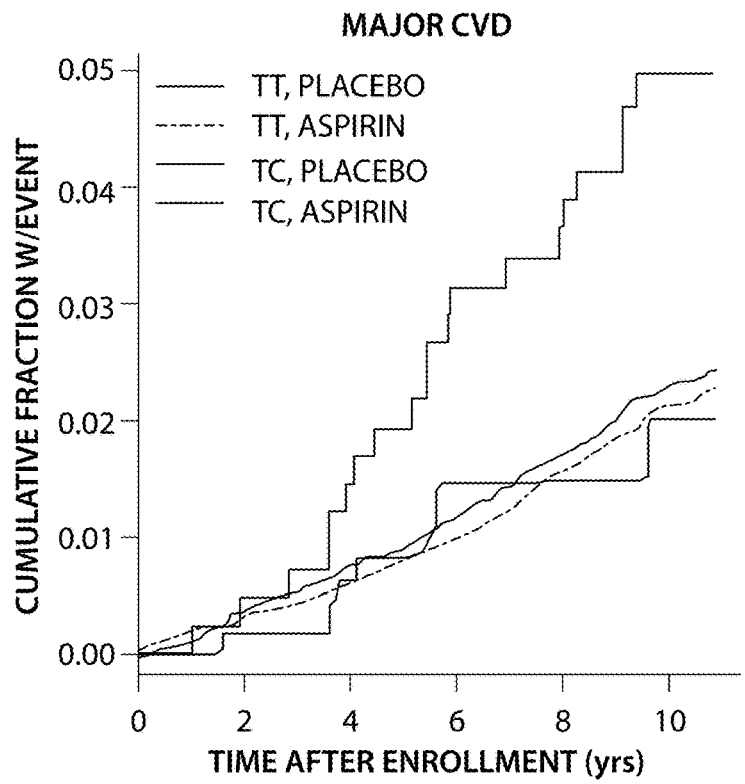
FIGS. 2A to 2D are sets of graphs showing the attenuation of risk from rs3798220 or elevated Lp(a) by aspirin therapy. Kaplan-Meier estimates of the cumulative fraction of Caucasian WHS participants with incident vascular disease FIG. 2A) stratified by rs3798220 genotype and aspirin or placebo assignment during the WHS trial for the composite endpoint of major vascular events, FIG. 2B) as in FIG. 2A) but for the endpoint of myocardial infarction, FIG. 2C) as in FIG. 2A) but for the endpoint of ischemic stroke, and FIG. 2D) among non-carriers of the minor allele of rs3798220 (TT genotype) stratified by Lp(a) levels above or below the $90^{th}$ percentile (65.1 mg/dL) and aspirin or placebo assignment for the composite endpoint of major vascular events.
Figure 2B:
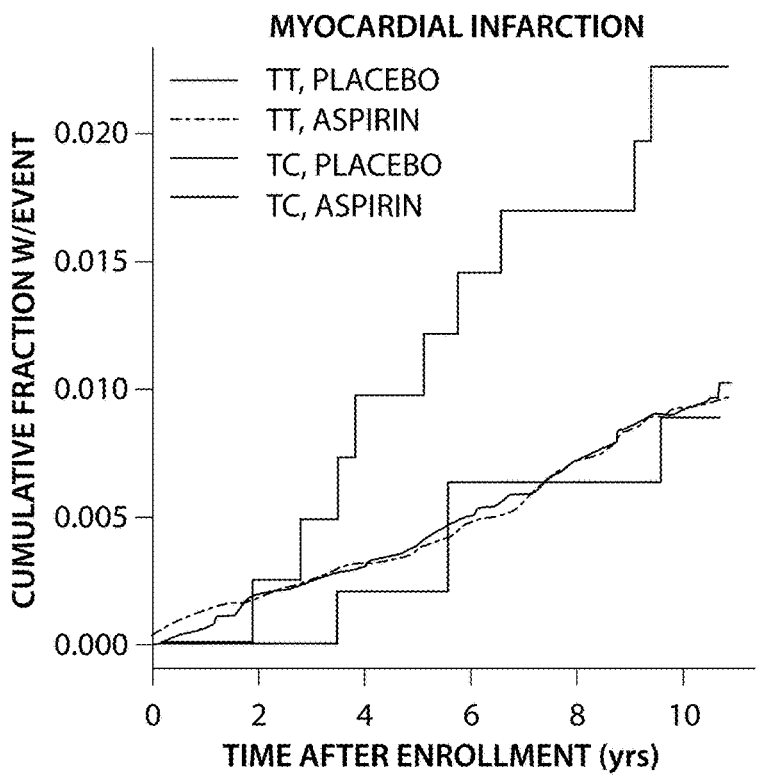
Figure 2C:
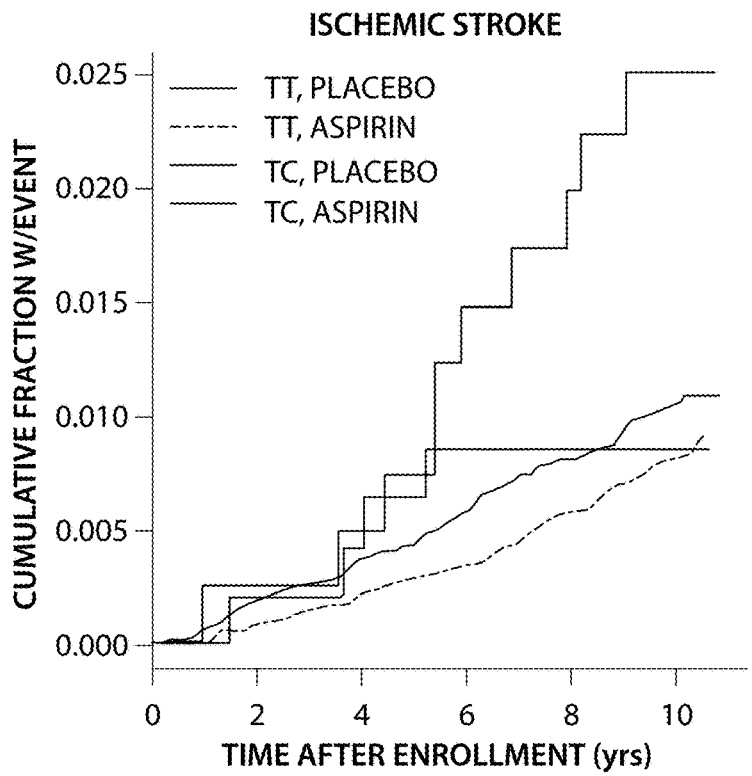

The increased risk of incident cardiovascular events among Caucasian heterozygotes of rs3798220 was largely negated by allocation to low dose aspirin treatment (FIGS. 2A-2D). Specifically, among heterozygotes, random assignment to aspirin was associated with a 59% reduction in relative risk of major vascular events (95% CI:0.81-0.10, p=0.025), whereas among non-carriers random allocation to aspirin had no significant effect (relative risk reduction 9%, 95% CI: 0.023 to −0.09, p=0.31) (FIG. 2A). Formally, this interaction of aspirin and genotype was significant (p=0.05, age-adjusted model). The differential effect of aspirin among genotype subgroups was also observed for the endpoints of MI and ischemic stroke (clinical events associated with acute plaque rupture and occlusive thrombosis). Thus, the net genetic effect for heterozygotes in the absence of aspirin was an approximate doubling of overall risk for major incident vascular events combined (age-adjusted HR 2.19, 95% CI: 1.39-3.46, p=0.0007), and separately for myocardial infarction (age-adjusted HR 2.43, 95% CI: 1.23-4.80, p=0.01) and ischemic stroke (age-adjusted HR 2.41, 95% CI: 1.26-4.59, p=0.008) (FIGS. 2A-2C). However, the effect of aspirin was attenuated for the endpoint of coronary revascularization (clinical events associated with underlying disease progression without acute occlusion; relative risk reduction 36%, 95% CI: 0.89 to −0.44, p=0.28).

Figure 2D:
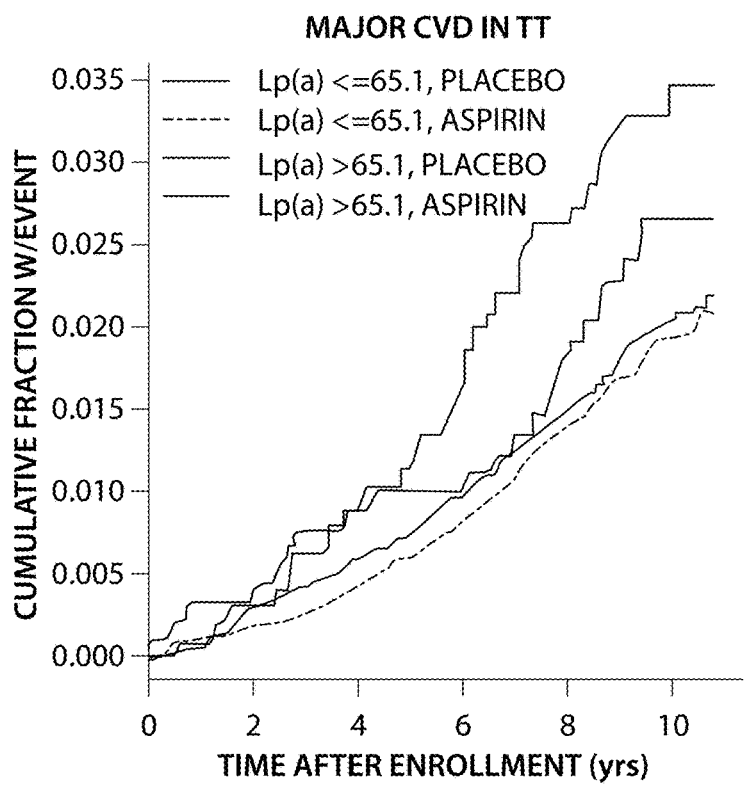

The interaction of aspirin with rs3798220 genotype appeared to be related in part to a similar interaction of aspirin with elevated Lp(a) levels in general. Among Caucasian non-carriers of the minor allele of rs3798220, aspirin reduced the relative risk of vascular events among those with Lp(a) levels above the 90th percentile (65.1 mg/dL) whereas minimal effect was observed among those with Lp(a) levels below the 90th percentile (FIG. 2D). For the revascularization endpoint, the aspirin effect among Caucasians with Lp(a) levels above the 90th percentile (relative risk reduction 39%, 95% CI: 0.64-0.05, p=0.03) was comparable in magnitude to the aspirin effect among Caucasian heterozygotes.

The prevalence of the minor allele of rs3798220 markedly differed between Caucasians (MAF=1.9%) and non-Caucasians in the WHS. Specifically, variation at rs3798220 was almost absent among self-identified African-Americans (MAF=0.5%). In contrast, the minor allele was more prevalent than among Caucasians for Asian-Americans (MAF=7.6%), Hispanics (MAF=15.1%), and Native Americans (MAF=9.1%) (Table 3). The differences in allele frequency compared with Caucasians were all significant, as were differences between African-Americans and Hispanics, Asian-Americans, or Native Americans and between Hispanics and Asians. The HapMap genotyping project detected the minor allele in Asians (CHB+JPT, MAF=5.6%) but not in Caucasians (CEU) or Africans (YRI) (37). The frequency among HapMap Asians was not significantly different from the frequency in the WHS Asian-American subpopulation (p=0.59). Among Caucasians, regional differences in allele frequency potentially related to varying degrees of admixture could not be detected by gross geographical classification across the US. In contrast to the finding in Caucasians, Lp(a) levels were neither elevated nor bimodal in the heterozygotes of the WHS Asian-American or Hispanic subpopulations, both of which had sufficient numbers of participants to evaluate the Lp(a) distribution. Similarly, there did not appear to be an association between rs3798220 and incident CVD in these populations, although power was limiting.

In this large-scale study of initially healthy women from the US, Caucasian carriers of the minor allele of the rs3798220 polymorphism in the apolipoprotein(a) gene (30) had greatly elevated levels of Lp(a) as well as a doubling of the risk of major vascular events. However, among heterozygotes randomly allocated to low-dose aspirin, this increased risk of future vascular events was effectively abolished (relative risk reduction with aspirin 59%, p=0.025). Among non-carriers, by contrast, there was minimal evidence of a benefit from aspirin therapy (relative risk reduction with aspirin 9%, p=0.31). In the context of the antithrombotic activity of aspirin, this pharmacogenetic result is consistent with a direct role of Lp(a) in thrombosis, perhaps through the plasminogen protease-like domain or lysine binding functions of the Kr domains as has been suggested previously (13, 38). The finding that the effects of aspirin on the association of rs3798220 with myocardial infarction and stroke are greater than its effects on coronary revascularization raises the intriguing possibility that an interplay between aspirin and Lp(a) derived from a particular apolipoprotein(a) allele may be more relevant for acute plaque rupture and vessel occlusion than disease progression. Whether or not the rs3798220 pharmacogenetic effect also involves possible allele-dependent reduction of apolipoprotein(a) expression by aspirin remains unknown (39, 40). Still, these data provide a direct genetic method for defining subpopulations with greater or lesser benefit from aspirin therapy, an issue pertinent to the controversial choice of aspirin or aspirin alternatives such as thienopyridines in the prevention and treatment of vascular disease (31, 41, 42).

The molecular basis of the complex relationship between the non-synonymous substitution encoded by rs3798220 and Lp(a) levels and cardiovascular risk will require further elucidation. In particular, the genetic effects on Lp(a) levels and distribution make it difficult to distinguish effects on risk and aspirin response solely related to increased Lp(a) levels from effects related to intrinsic biological activity imparted by the amino acid substitution, which may also contribute directly to elevated Lp(a). Similarly, relationships between rs3798220 and haplotypes at the apolipoprotein(a) locus are unclear, but may involve linkage to a high expressing allele of the apolipoprotein(a) locus in Caucasians, for example with an unusual number of type 2 Kringle IV domains (43, 44). This hypothesis might furthermore explain the bimodal pattern of the Lp(a) distribution, especially if rs3798220 is linked to two or more haplotypes directing different levels of Lp(a).

The allele frequency analysis is consistent with at least one origin of rs3798220 in Asia, but does not address the presence of this variant in Caucasians. Given the moderate frequency of rs3798220 in the Caucasians and the lack of apparent regional bias in its distribution across the US, admixture with Asian-American populations seems an unlikely explanation. However, while most variation private to non-African populations may have arisen through stochastic processes rather than positive selection (45), the association of rs3798220 with Lp(a) levels combined with its significantly different frequency in the Caucasians and other non-African populations raise the possibility that both selection and drift may be responsible for its biogeographic distribution. Both of these processes are consistent with the high level of population-specific genetic variation and expression at the apoliprotein(a) locus as well as speculation about Lp(a) function (3).

Aside from providing clues about the biological properties of Lp(a), the associations of rs3798220 with Lp(a) levels, cardiovascular risk, and the effect of aspirin treatment illustrate the potential of genetic approaches in understanding common complex disease. In this regard, the results offer not only a pharmacogenetic strategy for managing a specific type of CVD risk due to genetic variation but also the broader hope of administering healthcare with the highest possible precision through gene-based personalized medicine.

REFERENCES

1. S. M. Marcovina, M. L. Koschinsky, in *Handbook of lipoprotein testing* N. Rifai, G. R. Warnick, M. H. Dominiczak, Eds. (AACC Press, Washington, D.C., 2000) pp. 819.
2. L. Berglund, R. Ramakrishnan, *Arterioscler Thromb Vasc Biol* 24, 2219 (2004).
3. H. H. Hobbs, A. L. White, *Curr Opin Lipidol* 10, 225 (1999).
4. J. Danesh, R. Collins, R. Peto, *Circulation* 102, 1082 (2000).
5. P. M. Ridker, J. E. Buring, N. Rifai, N. R. Cook, *JAMA* 297, 611 (2007).
6. J. Suk Danik, N. Rifai, J. E. Buring, P. M. Ridker, *JAMA* 296, 1363 (2006).
7. G. L. Cushing et al., *Arteriosclerosis* 9, 593 (1989).
8. F. Paultre et al., *Arterioscler Thromb Vasc Biol* 20, 2619 (2000).
9. D. Baldassarre, E. Tremoli, G. Franceschini, S. Michelagnoli, C. R. Sirtori, *Stroke* 27, 1044 (1996).
10. F. Kronenberg et al., *Circulation* 100, 1154 (1999).
11. S. Tsimikas et al., *N Engl J Med* 353, 46 (2005).
12. M. B. Boffa, S. M. Marcovina, M. L. Koschinsky, *Clin Biochem* 37, 333 (2004).
13. M. A. Hancock, M. B. Boffa, S. M. Marcovina, M. E. Nesheim, M. L. Koschinsky, *J Biol Chem* 278, 23260 (2003).
14. N. M. Caplice et al., *Blood* 98, 2980 (2001).
15. R. Strater et al., *Lancet* 360, 1540 (2002).
16. E. Angles-Cano et al., *Chem Phys Lipids* 67-68, 369 (1994).
17. S. M. Marcovina, M. L. Koschinsky, *Curr Opin Lipidol* 14, 361 (2003).
18. B. R. Gabel, M. L. Koschinsky, *Biochemistry* 34, 15777 (1995).
19. U. Broeckel et al., *Nat Genet* 30, 210 (2002).
20. E. Boerwinkle et al., *J Clin Invest* 90, 52 (1992).
21. V. Mooser et al., *Am J Hum Genet* 61, 402 (1997).
22. K. Schmidt, H. G. Kraft, W. Parson, G. Utermann, *Eur J Hum Genet* 14, 190 (2006).
23. S. M. Marcovina, H. H. Hobbs, J. J. Albers, *Clin Chem* 42, 436 (1996).
24. S. M. Marcovina et al., *Clin Chem* 46, 1956 (2000).
25. S. M. Marcovina, M. L. Koschinsky, J. J. Albers, S. Skarlatos, *Clin Chem* 49, 1785 (2003).
26. O. Rosby, K. Berg, *J Intern Med* 247, 139 (2000).
27. K. Valenti, E. Aveynier, S. Leaute, F. Laporte, A. J. Hadjian, *Atherosclerosis* 147, 17 (1999).
28. J. P. Chretien et al., *J Med Genet* 43, 917 (2006).
29. R. Redon et al., *Nature* 444, 444 (2006).
30. M. M. Luke et al., submitted (2007).
31. P. M. Ridker et al., *N Engl J Med* 352, 1293 (2005).
32. C. N. Rotimi et al., *Genet Epidemiol* 14, 157 (1997).
33. J. Rubin et al., *J Lipid Res* 43, 234 (2002).

34. M. Scholz et al., *Eur J Hum Genet* 7, 169 (1999) page 17
35. H. G. Kraft et al., *Eur J Hum Genet* 4, 74 (1996).
36. C. Sandholzer et al., *Hum Genet* 86, 607 (1991).
37. The International HapMap Consortium, *Nature* 426, 789 (2003).
38. M. A. Hancock, C. A. Spencer, M. L. Koschinsky, *Biochemistry* 43, 12237 (2004).
39. M. Akaike et al., *Clin Chem* 48, 1454 (2002).
40. A. Kagawa, H. Azuma, M. Akaike, Y. Kanagawa, T. Matsumoto, *J Biol Chem* 274, 34111 (1999).
41. D. L. Bhatt et al., *Am Heart J* 150, 401 (2005).
42. M. A. Pfeffer, J. A. Jarcho, *N Engl J Med* 354, 1744 (2006).
43. D. Gavish, N. Azrolan, J. L. Breslow, *J Clin Invest* 84, 2021 (1989).
44. G. Utermann et al., *J Clin Invest* 80, 458 (1987).
45. D. A. Hinds et al., *Science* 307, 1072 (2005).

Materials and Methods

Study Populations: The primary study population derived from the Women's Health Study (WHS), a randomized trial of aspirin (100 mg orally on alternate days) and placebo in the primary prevention of cardiovascular disease conducted among initially healthy women aged at least 45 at enrollment who were followed over a 10 year period (1, 2). At enrollment, participants provided baseline clinical and demographic information. 28,345 WHS participants provided blood for plasma and genetic analysis. Among these samples, baseline Lp(a) levels were measured with a turbidimetric assay that is not affected by the number of Kr IV type-2 repeats on the Hitachi 917 analyzer (Roche Diagnostics, Indianapolis, Ind.) (3). Baseline measurement of other lipid fractions, inflammation biomarkers, and other plasma components has been described previously (4). Total incident cardiovascular events adjudicated during the follow-up period included those typically associated with plaque rupture and vessel occlusion such as myocardial infarction (MI), ischemic stroke, and cardiovascular death, as well as those typically associated with progression of underlying atherosclerotic disease defined as revascularization by percutaneous transluminal coronary angioplasty (PTCA) or coronary artery bypass graft (CABG). Major incident cardiovascular events were defined as myocardial infarction, ischemic stroke, or cardiovascular death. In addition, the association between rs3798220 and plasma Lp(a) levels was evaluated in an independent group of 1058 Caucasian men who had participated in the Physicians Health Study (PHS) (5). Among these PHS participants, Lp(a) levels were determined with a standard clinical ELISA-based method (6).

Genotyping: Genotypes for rs3798220 in the WHS participants were determined by an oligonucleotide ligation procedure that combined PCR amplification of target sequences from 3 ng of genomic DNA with subsequent allele-specific oligonucleotide ligation (7). The ligation products of the two alleles were then separated by hybridization to product specific oligonucleotides, each coupled to spectrally distinct Luminex®100™ xMAP microspheres (Luminex, Austin, Tex.). The captured products were fluorescently labeled with streptavidin R-phycoerythrin (Prozyme, San Leandro, Calif.), sorted on the basis of microsphere spectrum, and detected by a Luminex®100™ instrument (8). Genotypes at rs3798220 in the PHS were determined with a fluorescence-based, allele specific, real-time DNA amplification method as described (ABI, Foster City) (9). For the WHS and PHS populations respectively, the fractions of samples with successful genotype determination were 96.3% and 97.8%. Of the 27,289 women with DNA samples for genotyping, full ascertainment for rs3798220 genotype, Lp(a) levels, age, and occurrence of incident cardiovascular events were available for 25,436. Of these, 24,320 were Caucasian, 468 were African-American, 282 were Asian American, 262 where Hispanic, 62 were Native American, and 42 had unknown ancestry.

Statistical methods: Deviations from Hardy-Weinberg equilibrium were evaluated using a log-likelihood ratio test. Differences in clinical covariates among the three genotype classes were assessed by ANOVA procedures for normally-distributed characteristics, by the Kruskal-Wallis test for non-normally distributed characteristics, and by a Chi-Squared test of proportions for categorical characteristics. Similarly, the significance of differences in allele frequency between pairs of populations with different biogeographic ancestry was determined with a Chi-Squared test. For analysis of geographic bias in Lp(a) levels and in the minor allele frequency of rs3798220 alleles, place of residence at enrollment was classified into one of six groups corresponding to the northeast, south, midwest, southwest, mountain, and far west areas of the United States. The significance of these assignments in explaining Lp(a) levels or allele frequency was determined with logistic regression or chi-square analysis. Prospective assessment of the association between rs3798220 and the risk of incident CVD was performed with Cox proportional hazards models adjusted for age or traditional risk covariates (age, blood pressure, history of diabetes, smoking status, familial history of myocardial infarction, LDL-C, and HDL-C). In all reported analysis, the assumption of proportionality in the Cox models could not be rejected ($p > 0.05$). Differences in risk associated with aspirin treatment were determined either by including an interaction term in the Cox models or by analysis that stratified participants according to their assignment to aspirin or placebo.

Examination of Lp(a) levels among Caucasian rs3798220 heterozygotes revealed a clear bimodal distribution. One subgroup had lower Lp(a) levels with an approximately log-normal distribution that is also observed for non-carriers of the minor allele, while the other subgroup had higher Lp(a) levels with an approximate normal distribution. Therefore, these participants were classified into low or high Lp(a) subgroups by modeling the observed bimodal distribution as a mixture of independent log-normal [for low Lp(a)] and normal [for high Lp(a)] distributions that were fit to Lp(a) values with an expectation maximization (EM) algorithm (10). An Lp(a) level of 27.9 mg/dL corresponding to a responsibility value of 0.5 in the EM algorithm was used to discriminate the high Lp(a) group from the low Lp(a) group. The classification with this two-distribution model was essentially unambiguous in that of 806 assignments out of 887 (91%) had responsibility values that were at least 95% of certainty.

REFERENCES FOR MATERIALS AND METHODS

1. I. M. Lee et al., *JAMA* 294, 56 (2005).
2. P. M. Ridker et cd., *N Engl J Med* 352, 1293 (2005).
3. S. M. Marcovina et al., *Clin Chem* 46, 1956 (2000).
4. P. M. Ridker, N. Rifai, N. R. Cook, G. Bradwin, J. E. Buring, *JAMA* 294, 326 (2005).

5. R. Y. Zee, S. Cheng, H. H. Hegener, H. A. Erlich, P. M. Ridker, *Stroke* 37, 2007 (2006).
6. P. M. Ridker, C. H. Hennekens, M. J. Stampfer, *JAMA* 270, 2195 (1993).
7. F. Barany, *Proc Natl Acad Sci USA* 88, 189 (1991).
8. S. A. Dunbar, *Clin Chim Acta* 363, 71 (2006).
9. J. B. de Kok, E. T. Wiegerinck, B. A. Giesendorf, D. W. Swinkels, *Hum Mutat* 19, 554 2002.
10. T. Hastie, R. Tibshirani, J. Friedman, *The elements of statistical learning* (Springer-Verlag, New York, 2001), pp. 533.

TABLE 1

Baseline clinical profile for Caucasian WHS participants by genotype

| | rs3798220 genotype* | | | |
|---|---|---|---|---|
| | TT (N = 24119) | TC (N = 904) | CC (N = 15) | p-value |
| Clinical characteristics | | | | |
| age (yrs.) | 52 (48.0-59.0) | 52.0 (48-0-58.0) | 52 (49.5-55.0) | 0.352 |
| BMI (kg/m^2) | 24.9 (22.5-28.3) | 24.7 (22.4-28.3) | 24.9 (22.1-28.9) | 0.758 |
| history hypertension (%) | 5950 (24.7) | 237 (26.2) | 3 (20.0) | 0.530 |
| family history MI (%) | 2801 (12.9) | 127 (15.5) | 2 (15.4) | 0.077 |
| current smoking (%) | 2795 (11.6) | 109 (12.1) | 2 (13.3) | 0.912 |
| diabetes (%) | 614 (2.5) | 22 (2.4) | 0 (0.0) | 0.944 |
| HRT (%) | 10472 (43.5) | 419 (46.5) | 9 (60.0) | 0.100 |
| menopause (%) | 13139 (54.6) | 486 (53.8) | 8 (53.3) | 0.907 |
| Lipid biomarkers | | | | |
| total cholesterol (mg/dL) | 208.0 (184.0-235.0) | 215.0 (189.0-241.0) | 229 (208.5-250.0) | 0.00031# |
| LDL-C (mg/dL) | 121.3 (100.4-144.2) | 126.5 (105.5-149.2) | 137.6 (118.8-157.4) | 0.00022# |
| apolipoprotein B (mg/dL) | 100.0 (83.8-121.3) | 107.3 (87.1-125.1) | 109.8 (100.4-127.0) | 0.00001# |
| HDL-C (mg/dL) | 51.8 (43.1-62.2) | 51.8 (43.5-62.4) | 51.7 (46.0-66.8) | 0.600 |
| apolipoprotein AI (mg/dL) | 148.9 (132.3-167.9) | 148.2 (133.4-166.3) | 145.2 (135.9-168.3) | 0.983 |
| triglycerides (mg/dL | 119 (84-176) | 117.0 (83.0-177.2) | 104 (90.0-149.0) | 0.890 |
| Lp(a) (mg/dL) | 10.0 (4.2-28.5) | 79.3 (13.7-102.1) | 153.9 (105.6-215.0) | <<0.001+ |
| Inflammation biomarkers | | | | |
| C-reactive protein (mg/L) | 2.0 (0.8-4.4) | 2.0 (0.8-4.2) | 1.1 (0.9-2.4) | 0.342 |
| soluble ICAM-1 (ng/ml) | 342.9 (301.8-394.8) | 343.8 (301.4-396.4) | 349.4 (295.6-399.2) | 0.961 |
| fibrinogen (mg/L) | 349.9 (307.0-401.1) | 348.9 (307.6-401.7) | 343.5 (318.4-382.7) | 0.851 |
| Other biomarkers | | | | |
| creatinine (mg/dL) | 0.7 (0.6-0.8) | 0.7 (0.6-0.8) | 0.7 (0.7-0.8) | 0.402 |
| homocysteine (umol/dL) | 10.5 (8.7-12.9) | 10.5 (8.7-12.8) | 11.6 (8.6-12.7) | 0.468 |
| HbA1c (%) | 5.0 (4.8-5.2) | 5.0 (5.8-5.2) | 4.9 (4.8-5.2) | 0.658 |

*Median (inter-quartile range for quantitative characteristics of N (%) for discrete characteristics.
+Analytic p = $4.7 \times 10^{-177}$
Not significant after adjustment for Lp(a) levels.

TABLE 2

Association of rs3798220 with cardiovascular events among Caucasians

| | | | | rs3798220 genotype and Lp(a) levels | | | |
|---|---|---|---|---|---|---|---|
| | | | | high Lp(a) | | low Lp(a) | |
| | nts | HR CI) | p | HR CI) | p | HR CI) | p |
| Total incident CVD | 825 | 1.502.05) | 0.012 | 1.782.51) | 0.001 | 0.841.77) | 0.650 |
| Major incident CVD | 521 | 1.582.33) | 0.021 | 1.852.83) | 0.005 | 0.962.33) | 0.930 |
| Myocardial infarction | 211 | 1.572.88) | 0.150 | 1.833.57) | 0.076 | 0.953.83) | 0.940 |
| Ischemic stroke | 221 | 1.813.17) | 0.039 | 2.013.79) | 0.031 | 1.364.25) | 0.600 |
| Revascularization | 475 | 1.432.18) | 0.092 | 1.792.80) | 0.011 | 0.621.93) | 0.410 |

Cox proportional hazards models comparing heterozygotes to the reference homozygotes for major allele genotype (TT), including adjustments for age.

TABLE 3

Minor allele frequency of rs3798220 in WHS and HapMap subpopulations

| | | | | p-value for pairwise difference in MAF | | | | | | |
|---|---|---|---|---|---|---|---|---|---|---|
| group | N+ | MAF | HWEp | Hisp. | A. Am | As | N. Am | CHB + JPT | CEU | YRI |
| WHS all | 26495 | 0.021 | 0.002 | — | — | — | — | — | — | — |
| WHS Caucasian | 25038 | 0.019 | 0.048 | <0.001 | 0.001 | <0.001 | 0.001 | <0.001 | 0.002 | 0.002 |
| WHS Hispanic | 275 | 0.151 | 0.901 | — | <0.001 | <0.001 | 0.017 | 0.005 | 0.000 | 0.000 |
| WHS African-American | 486 | 0.005 | 0.872 | — | — | <0.001 | 0.001 | <0.001 | 0.274 | 0.272 |
| WHS Asian | 360 | 0.076 | 0.940 | — | — | — | 0.244 | 0.593 | 0.005 | 0.005 |
| WHS Native American | 66 | 0.091 | 0.273 | — | — | — | — | 0.808 | 0.004 | 0.005 |
| HapMap CHB + JPT | 89 | 0.056 | 0.440 | — | — | — | — | — | 0.056 | 0.055 |
| HapMap CEU | 60 | 0.000 | — | — | — | — | — | — | — | NA |
| HapMap YRI | 60 | 0.000 | — | — | — | — | — | — | — | — |

+Number of individuals in each subpopulation with successful genotype for rs3798220
NA, not applicable

Example 2: Genotyping of 40 Additional SNPs at and Near the LPA Locus in WHS Samples to Determine SNP Variation in LD with Rs3798220 in European-Americans, Asian-Americans, and American Hispanics We genotyped 40 additional SNPs at LPA (the gene for apolipoprotein (a)) and neighboring loci in a subset of samples from the WHS chosen on the basis of both rs3798220 genotype and self-reported ancestry (European-American (i.e., White or Caucasian), Asian-American, or American Hispanic). We then estimated linkage disequilibrium (LD) between these new SNPs and rs378220. Because the samples were not chosen at random but instead on the basis of rs3798220 genotype, we could not simply estimate allele frequency and LD from the sample directly but had to infer allele frequencies and LD by minimizing the difference between the observed and predicted genotypes given the rs379220-based sampling strategies. The results showed that:

1) two SNPs (rs9457931 dbSNP@NCBI (single nucleotide polymorphism at position chromosome 6:160849894 NCBI build 128) and rs9457927 dbSNP@NCBI (single nucleotide polymorphism at position chromosome 6:160830272 NCBI build 128)) were in almost complete LD with rs3798220 among the WHS Caucasians (European-Americans). Both SNPs are in neighboring LPAL2 gene (lipoprotein, Lp(a)-like 2 precursor gene, adjacent to the gene for apolipoprotein(a));

2) other SNPs have a range of LD to rs3798220; and 3) there is a very different pattern of LD in the non-European sub-populations. We interpret these results to suggest that the effects we described in Example 1 are related to an allele carrying all three SNPs (rs3798220, rs9457931, rs9457927).

Figure 3A:
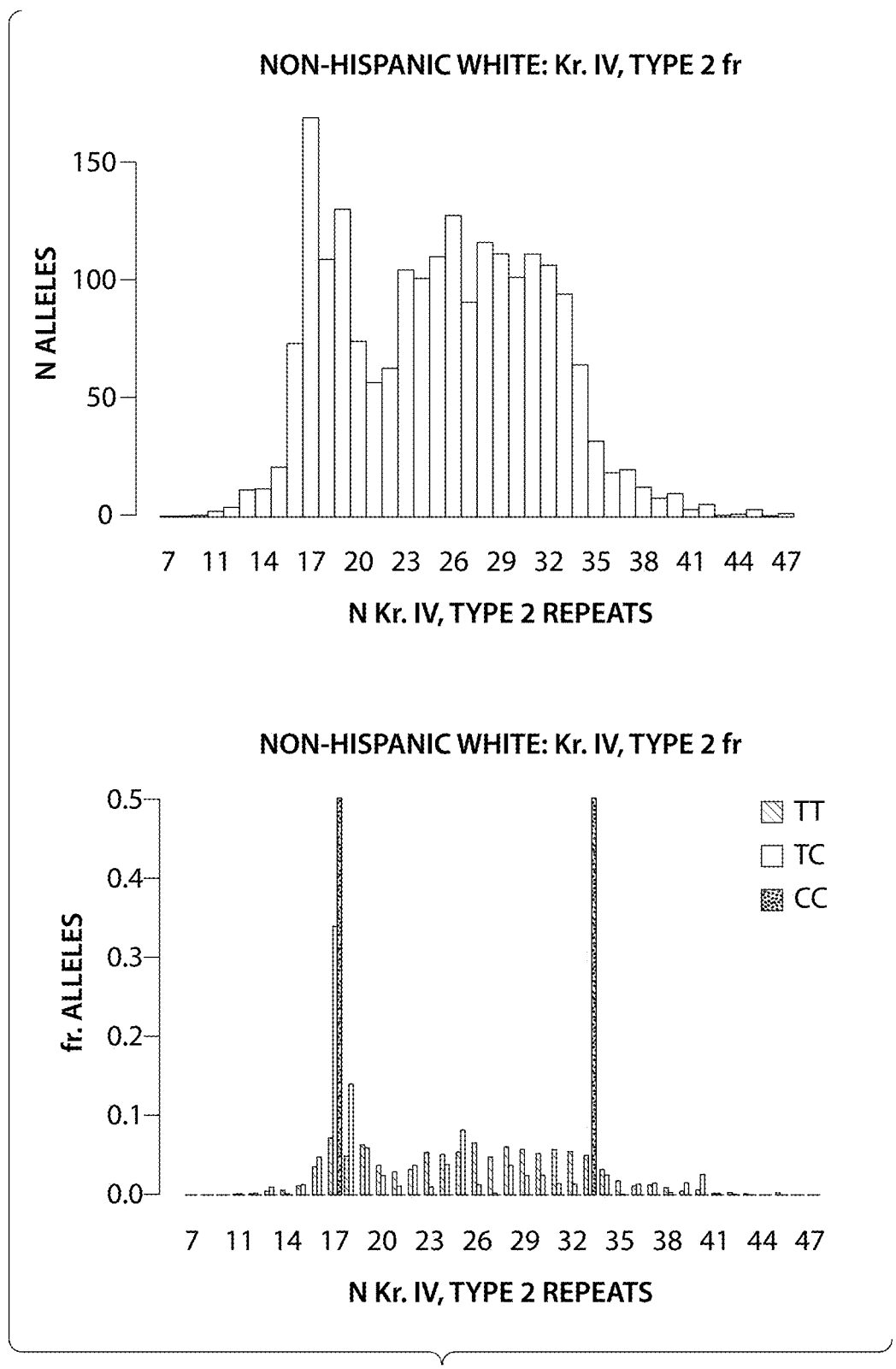
FIGS. 3A to 3B are sets of histograms showing distribution of KrIV2r number among non-Hispanic whites.
Figure 3B:
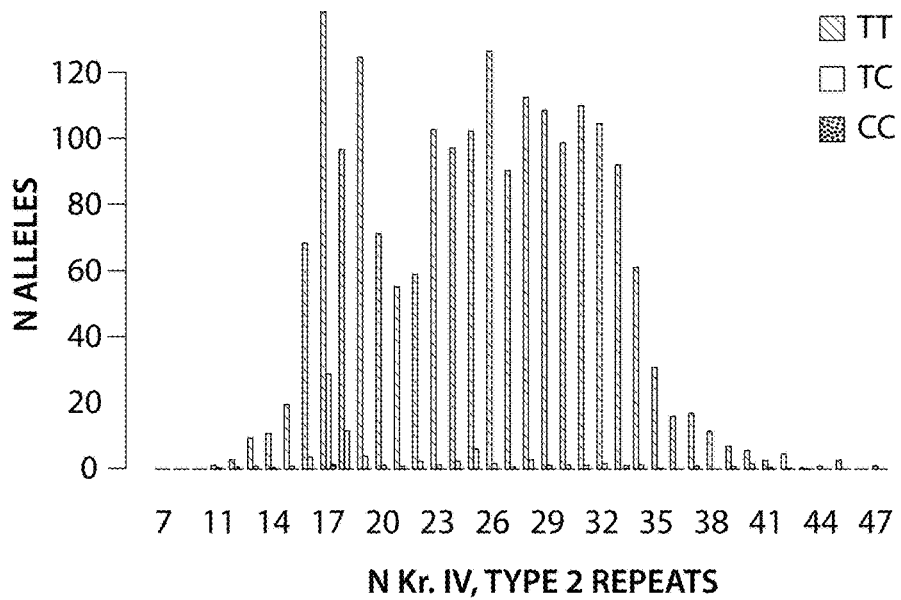
Figure 4:
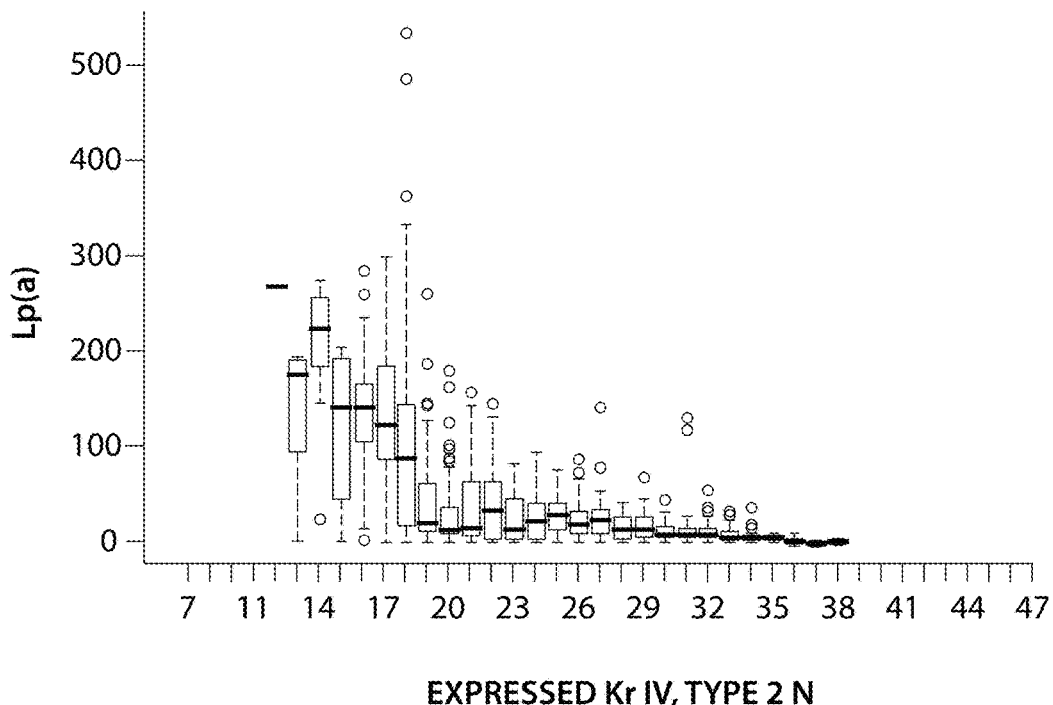
FIG. 4 is a plot showing the distribution of Lp(a) level according to number of KrIV2r's among non-Hispanic whites.
Figure 5:
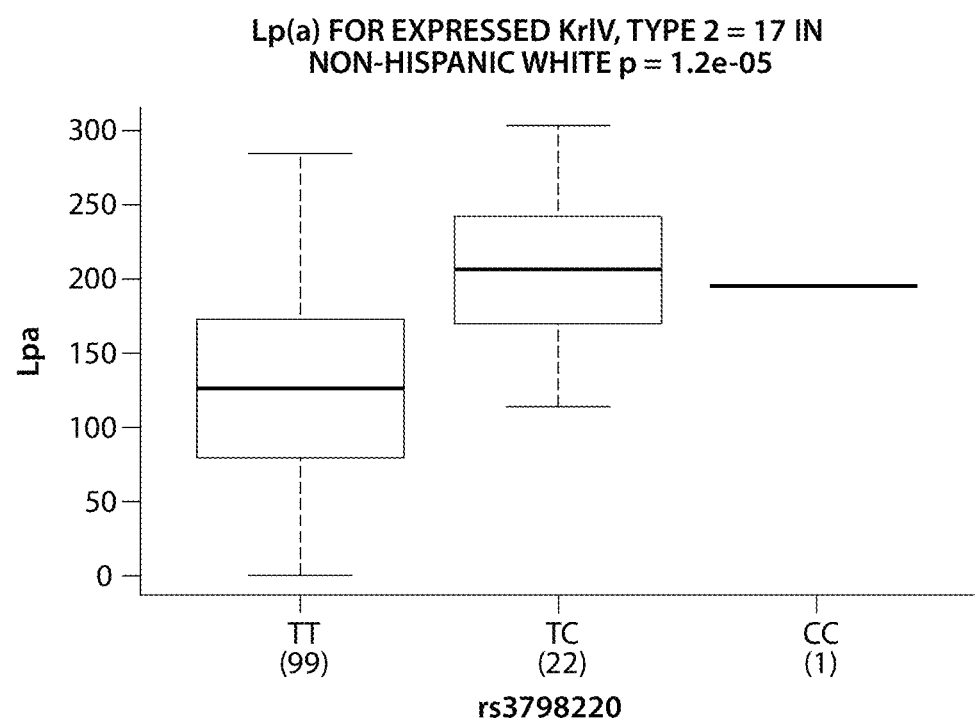
FIG. 5 is a plot showing the numbers of KrIV2r's (i.e. alleles) with significantly different levels of Lp(a) according to rs3798220 genotype among non-Hispanic whites.

Example 3: Relationship Between Rs3798220 Genotype, Number of Kringle IV Type 2 Repeats and Lp(a) Expression in Three Sub-Groups from the Dallas Heart Study with Distinct Ancestry We had rs3798220 genotyped in Dallas Heart Study (DHS) (The American Journal of Cardiology Volume 93, Issue 12, 15 Jun. 2004, Pages 1473-1480) for which the number of Kr IV, type 2 repeats (KrIV2r's) in the apolipoprotein(a) component of plasma Lp(a) (i.e. expressed apop (a) protein) had been determined previously (Circulation. 2005; 111:1471-1479). This population includes both men and women, among non-Hispanic Whites (European ancestry), Blacks (African ancestry), and Hispanics, totaling 3529 samples. The analysis sought to identify a correspondence between the minor allele of rs3798220 and the number of expressed KrIV2r's, with possible dependence on ancestry. The analysis was performed the analysis two ways. In the first, all individuals were considered, and each individual's KrIV2r alleles (at the DNA level) were assumed to be equivalent to the expressed alleles (at the protein level). That is, individuals with only one KrIV2r expressed were assumed to have two copies of that allele at the LPA locus (3529 individuals). In the second, we considered only individuals with two clearly distinct KrIV2r alleles (2859 total), excluding 668 with only one KrIV2r allele expressed from analysis. The conclusions were very similar for both. Namely, 1) among non-Hispanic whites, the minor allele of rs3798220 was strongly correlated with 17 KrIV2r repeats and to a lesser extent 16 or 18 repeats (although the difference between 16, 17 and 18 repeats could relate to the resolution of the assay for KrIV2r number) (FIGS. 3A-3B); 2) among non-Hispanic whites, alleles with a smaller number of KrIV2r's generally express higher levels of Lp(a) (FIG. 4); 3) while non-Hispanic whites expressing 17 KrIV2r's have high levels of Lp(a), individuals who, in addition, also carry one copy of the minor allele of rs3798220 have significantly even higher levels of Lp(a) (page 11, lower right) (FIG. 5); and 4) the distribution of KrIV2r's, their correlation with expression level, and their correlation with rs3798220 is different in the different ancestral groups so that correlation of rs3798220 and extreme levels of Lp(a) observed non-Hispanic whites is not observed in the groups of the other ancestries.

We claim:

1. A method comprising:
   (a) determining the identity of a single nucleotide polymorphism at position chromosome 6:160880877 (March 2006 assembly—NCBI build 36.1; rs3798220 dbSNP @ NCBI) of an apolipoprotein(a) (Apo(a)) gene in a human subject,
   wherein the presence of cytosine or guanine at position chromosome 6:160880877 indicates responsiveness to acetylsalicylic acid,
   wherein the presence of thymine or adenine at position chromosome 6:160880877 indicates non-responsiveness to acetylsalicylic acid; and
   (b) administering acetylsalicylic acid to a human subject responsive to acetylsalicylic acid to reduce the risk of a cardiovascular event, or
   administering an antiplatelet or antithrombotic agent that is not acetylsalicylic acid to a human subject non-responsive to acetylsalicylic acid to reduce the risk of a cardiovascular event.

2. The method of claim 1, further comprising determining a level of Lipoprotein(a) (Lp(a)) in a blood sample from the subject.

3. The method of claim 2, wherein the subject has an elevated level of Lp(a) in the blood.

4. The method of claim 3, wherein the level of Lp(a) is about 10 mg/dl or higher in the blood sample from the subject.

5. The method of claim 3, wherein the level of Lp(a) is about 15 mg/dl or higher in the blood sample from the subject.

6. The method of claim 3, wherein the level of Lp(a) is about 20 mg/dl or higher in the blood sample from the subject.

7. The method of claim 3, wherein the level of Lp(a) is about 25 mg/dl or higher in the blood sample from the subject.

8. The method of claim 1, wherein the cardiovascular event is myocardial infarction, stroke, acute coronary syndrome, myocardial ischemia, chronic stable angina pectoris, unstable angina pectoris, cardiovascular death, coronary re-stenosis, coronary stent re-stenosis, coronary stent re-thrombosis, revascularization, angioplasty, transient ischemic attack, pulmonary embolism, vascular occlusion, or venous thrombosis.

9. The method of claim 1, wherein the identity of the polymorphism is determined by contacting a nucleic acid obtained from the subject with a nucleic acid probe.

10. The method of claim 1, wherein the identity of the polymorphism is determined by allele-specific probe hybridization, allele-specific primer extension, allele-specific amplification, 5' nuclease digestion, molecular beacon assay, oligonucleotide ligation assay, size analysis, or single-stranded conformation polymorphism.

11. The method of claim 1, wherein the identity of the polymorphism is determined by sequencing a nucleic acid obtained from the subject.

12. A method of treatment comprising:
   selecting a human subject on the basis that the human subject has an Apo(a) polymorphism characterized by cytosine or guanine at chromosome 6:160880877 (March 2006 assembly—NCBI build 36.1; rs3798220 dbSNP @ NCBI), and
   administering to the human subject acetylsalicylic acid, thereby reducing the risk of a future cardiovascular event.

13. The method of claim 12, wherein the human subject also has an elevated level of Lipoprotein(a) (Lp(a)) in the blood.

14. The method of claim 13, wherein the level of Lp(a) is about 10 mg/dl or higher in a blood sample from the subject.

15. The method of claim 14, wherein the level of Lp(a) is about 15 mg/dl or higher in a blood sample from the subject.

16. The method of claim 12, wherein the cardiovascular event is myocardial infarction, stroke, acute coronary syndrome, myocardial ischemia, chronic stable angina pectoris, unstable angina pectoris, cardiovascular death, coronary re-stenosis, coronary stent re-stenosis, coronary stent re-thrombosis, revascularization, angioplasty, transient ischemic attack, pulmonary embolism, vascular occlusion, or venous thrombosis.

* * * * *

SEQUENCE LISTING

<160> NUMBER OF SEQ ID NOS: 5

<210> SEQ ID NO 1
<211> LENGTH: 51

```
<212> TYPE: DNA
<213> ORGANISM: Homo sapiens

<400> SEQUENCE: 1
gctccaagaa cagcctagac acttccattt cctgaacatg agattcgagg t            51

<210> SEQ ID NO 2
<211> LENGTH: 51
<212> TYPE: DNA
<213> ORGANISM: Homo sapiens

<400> SEQUENCE: 2
cgaggttctt gtcggatctg tgaaggtaaa ggacttgtac tctaagctcc a            51

<210> SEQ ID NO 3
<211> LENGTH: 51
<212> TYPE: DNA
<213> ORGANISM: Homo sapiens

<400> SEQUENCE: 3
gctccaagaa cagcctagac acttctattt cctgaacatg agattcgagg t            51

<210> SEQ ID NO 4
<211> LENGTH: 51
<212> TYPE: DNA
<213> ORGANISM: Homo sapiens

<400> SEQUENCE: 4
cgaggttctt gtcggatctg tgaagataaa ggacttgtac tctaagctcc a            51

<210> SEQ ID NO 5
<211> LENGTH: 23
<212> TYPE: DNA
<213> ORGANISM: Artificial Sequence
<220> FEATURE:
<223> OTHER INFORMATION: Synthetic

<400> SEQUENCE: 5
cgaatctcat gttcaggaaa ata                                           23
```